United States Patent
Tagawa et al.

(10) Patent No.: US 6,951,911 B2
(45) Date of Patent: Oct. 4, 2005

(54) CROSS-LINKED POLYMER AND PROCESS FOR PRODUCING THE SAME, ABSORPTIVE STRUCTURE AND ABSORPTIVE ARTICLE

(75) Inventors: Daisuke Tagawa, Kyoto (JP); Tatsuya Asai, Kyoto (JP); Yoshiyuki Iwasaki, Kyoto (JP); Yoshihisa Ota, Kyoto (JP); Keiji Tanaka, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 174 days.

(21) Appl. No.: 10/272,393

(22) Filed: Oct. 15, 2002

(65) Prior Publication Data

US 2003/0078349 A1 Apr. 24, 2003

Related U.S. Application Data

(63) Continuation of application No. PCT/JP01/03138, filed on Apr. 11, 2001.

(30) Foreign Application Priority Data

Apr. 13, 2000 (JP) ........................................ 2000-111703
Apr. 13, 2000 (JP) ........................................ 2000-111747
Mar. 10, 2001 (JP) ........................................ 2001-073606

(51) Int. Cl.$^7$ ............................................. C08F 120/06
(52) U.S. Cl. .................... 526/317.1; 526/137; 526/139; 526/141; 526/169; 526/172; 526/271; 526/287; 526/320; 526/328.5; 526/347; 525/327.4; 525/328; 525/329.5; 525/33; 428/500; 428/913; 442/59
(58) Field of Search .................... 526/137, 139, 526/347, 141, 169, 172, 271, 287, 317.1, 320, 328.5; 525/327.4, 328, 329.5, 33; 442/59; 428/500, 913

(56) References Cited

U.S. PATENT DOCUMENTS

| | | | | |
|---|---|---|---|---|
| 4,090,013 A | * | 5/1978 | Ganslaw et al. | ......... 525/329.9 |
| 4,769,427 A | * | 9/1988 | Nowakowsky et al. | ....... 526/64 |
| 5,145,906 A | | 9/1992 | Chambers et al. | |
| 5,380,808 A | | 1/1995 | Sumiya et al. | |
| 5,669,894 A | * | 9/1997 | Goldman et al. | ............ 604/368 |
| 6,392,116 B1 | * | 5/2002 | Beihoffer et al. | ............ 604/372 |
| 6,562,879 B1 | * | 5/2003 | Hatsuda et al. | ................ 521/56 |

FOREIGN PATENT DOCUMENTS

| | | | |
|---|---|---|---|
| EP | 0 618 005 B1 | 3/1994 | ............ B01J/20/26 |
| JP | 01-113406 | 5/1989 | ............. C08F/8/00 |
| JP | 03-179008 | 8/1991 | ........... C08F/20/06 |
| JP | 06-287220 | 10/1994 | ............. C08F/8/30 |
| JP | 2000-26510 A | 1/2000 | |
| JP | 2000-026510 | 1/2000 | ............. C08F/2/16 |
| WO | PCT WO 91/18031 | 11/1991 | ......... C08F/220/04 |

* cited by examiner

*Primary Examiner*—Helen L. Pezzuto
(74) *Attorney, Agent, or Firm*—Peters, Verny, Jones, Schmitt & Aston, L.L.P.; Howard M. Peters

(57) ABSTRACT

A crosslinked polymer (A) which comprises, as essential structural units, units derived from (a) one or more vinyl monomers selected from the group consisting of water-soluble vinyl monomers and/or vinyl monomers which become water-soluble upon hydrolysis and units derived from (b) a crosslinking agent and which satisfies the following requirements: (1): (X)≧25 g/g, (2): (Y)≧15 g/g, and (3): (Y)≧−0.54 (X)+41. It has exceedingly high water retentivity and exceedingly high absorbing power under load. When applied to an absorbent structure and an absorbent article, the polymer has excellent absorbing performance. In the relationships, (X) is the amount of physiological saline retained through 1-hour absorption and (Y) is the amount of physiological saline absorbed through 1-hour standing under a load of 60 g/cm$^2$.

26 Claims, No Drawings

CROSS-LINKED POLYMER AND PROCESS FOR PRODUCING THE SAME, ABSORPTIVE STRUCTURE AND ABSORPTIVE ARTICLE

RELATED APPLICATIONS

This application is a continuation of International Application Ser. No PCT/JP01/03138, filed Apr. 11, 2001, and continuation-in-part applications of Japanese Serial Nos. 2000-111703, filed Apr. 13, 2000; 2000-11747, filed Apr. 12, 2000 and 2001-073606, filed Mar. 15, 2001, all of which are incorporated herein by reference in their entirety. All U.S. patents cited herein are incorporated by reference in their entirety.

BACKGROUND OF THE INVENTION

1. Technical Field

The present invention relates to a cross-linked polymer and a process for producing the same, an absorptive structure and an absorptive article. More particularly, the present invention relates to a cross-linked polymer having the extremely excellent water-retaining capacity and absorbing capacity under load and a process for producing the same, an absorptive structure and an absorptive article.

2. Background Techniques

Previously, it has been demanded that cross-linked polymers used in absorbing articles such as a paper diaper have the large water retaining amount and the large absorbing amount under load, and many improvements have been tried by a number of methods. As a method for enhancing the water retaining amount, there have been proposed a method of using a chain transfer agent such as a thiol compound (JP-A 3-179008) and the like in addition to the method of optimization by varying an amount of an polymerization initiator, a polymerization temperature, a polymerization concentration and the like. On the other hand, as a method for enhancing the absorbing capacity under load, there has been proposed a number of methods of treating a part near the surface of a polymerized particle (JP no. 267529, EPA618005 etc.)

However, according to these methods, the properties are necessarily biased, a cross-linked polymer does not satisfy both the water retaining capacity and absorbing capacity under load at the same time and, for this reason, when used in absorbing article, the absorbing capacity is not sufficient and, thus, further improvement is desired. The present inventors studied intensively in order to obtain a cross-linked polymer exhibiting the excellent absorbing capacity when used in absorbing article, which resulted in completion of the present invention:

An object of the present invention is to provide a cross-linked polymer satisfying both water retaining capacity and absorbing capacity under load at the same time and a process for producing the same. Another object of the present invention is to provide an absorptive structure and absorptive article exhibiting the excellent absorbing capacity when the present cross-linked polymer is applied to hygiene articles such as physiological napkins.

SUMMARY OF THE INVENTION

The present invention provides the following inventions (I) to (IV):

(I) a cross-linked polymer (A), which comprises 1 or 2 or more vinyl series monomers (a) selected from the group consisting of a water-soluble vinyl series monomer and/or a monomer which become water-soluble by hydrolysis and a cross-linking agent (b) as an essential component, wherein said cross-linked polymer satisfies the following requirements ① to ③:
① $(X) \geq 33$ g/g,
② $(Y) \geq 25$ g/g,
③ $(Y) \geq -0.54(X) + 42$
wherein, (X) is a water retaining amount for a physiological saline after 1 hour absorption, and (Y) is an absorbing amount under 60 g/cm² load for a physiological saline after 1 hour, saline after 1 hour, (II) a process for producing a cross-linked polymer (A), which comprises polymerizing 1 or 2 or more vinyl series monomers (a) selected from the group consisting of a water-soluble vinyl series monomer and/or a monomer which become water-soluble by hydrolysis and, if necessary, another vinyl series monomer (a3), and a first cross-linking agent (b1) in the presence of 1 or 2 or more initiators (C) selected from the group consisting of an azo series initiators, a peroxide series initiator, a redox series initiator and an organic halogenated compound initiator and water, to obtain a cross-linked polymer (A2), which is further surface-cross-linked with a second cross-linking agent (b2), (III) an absorptive structure (C) comprising a matrix composed of the cross-linked polymer (A) and a fibrous material (B), wherein an amount of the cross-linked polymer (A) is 30 to 95% by weight relative to the absorptive structure (C), and (IV) an absorptive article comprising the absorptive structure (C), a liquid permeable sheet and a breathable back sheet.

DETAILED DESCRIPTION OF THE INVENTION (A Cross-Linked Polymer and a Process for Producing the Same)

In the present invention, the water-soluble vinyl series monomer and/or a vinyl monomer which becomes water-soluble by hydrolysis (a) are not particularly limited, but examples of the water-soluble vinyl series monomer (a1) include vinyl series monomers having at least 1 hydrophilic group such as acidic group and/or its salt forming group [carboxylic acid (carboxylate) group, sulfonic acid (sulfonate) group, sulfuric acid (sulfate) group, phosphoric acid (phosphate) group etc.], hydorxy group, amido group, amino group, quaternary ammonium salt group and the like, and they are classified into anionic, nonionic and cationic monomers as follows:

(i) Anionic vinyl series monomers or vinyl series monomers which become anionic (i-1) Examples of monomers having a carboxylic acid group include monomers having the carbon number of 3 to 30, for example, carboxyl group-containing vinyl series monomers such as unsaturated monocarboxylic acids such as (meth)acrylic acid, crotonic acid and cinnamic acid; unsaturated dicarboxylic acids such as maleic acid, fumaric acid, citraconic acid, itaconic acid and the like; monoalkyl (carbon number of 1 to 8) esters of unsaturated dicarboxylic acids (as described above) such as maleic acid monobutyl ester, fumaric acid monobutyl ester, maleic acid ethylcarbitol monoester, fumaric acid ethylcarbitol monoester, citraconic acid monobutyl ester, itaconic acid glycol monoester and the like, and a combination of 2 or more of them.

(i-2) Examples of vinyl series monomers having a sulfonic acid group include aliphatic or aromatic vinylsulfonic acids having the carbon number of 2 to 30, such as vinylsulfonic acid, (meth)allylsulfonic acid; styrenesulfonic acid, α-methylstyrenesulfonic acid; (meth)acrylalkylsulfonic acids [(meth)acryloxypropylsulfonic acid, 2-hydroxy-3-

(meth)acryloxypropylsulfonic acid, 2-(meth)acryloylamino-2,2-dimethylethanesulfonic acid, 3-(meth)acryloxyethanesulfonic acid, 2-(meth)acrylamido-2-methylpropanesulfonic acid, 3-(meth)acrylamido-2-hydroxypropanesulfonic acid]; alkyl (carbon number of 3 to 18) (meth)allylsulfosuccinic acid ester and the like.

(i-3) Examples of vinyl series monomers having a sulfuric acid group or a sulfate include sulfate of hydroxyalkyl (carbon number of 2 to 6) (meth)acrylate [sulfate of hydroxyethyl (meth)acrylate etc.]; sulfate of poly(n=2–30) oxyalkylene(carbon number of 2–4:alone, random or block) mono(meth)acrylate [sulfate of poly(n=5–15)oxypropyrene monomethacrylate etc.]; compounds represented by the following formulas (1), (2) and (3):

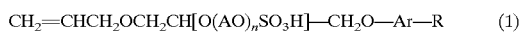

$$CH_2=CHCH_2OCH_2CH[O(AO)_nSO_3H]-CH_2O-Ar-R \qquad (1)$$

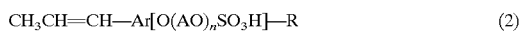

$$CH_3CH=CH-Ar[O(AO)_nSO_3H]-R \qquad (2)$$

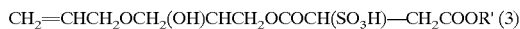

$$CH_2=CHCH_2OCH_2(OH)CHCH_2OCOCH(SO_3H)-CH_2COOR' \qquad (3)$$

In the formula (1) to (3), R represents an alkyl group having the carbon number of 1 to 15; R' represents an alkyl group having the carbon number of 1 to 15 optionally substituted with fluorine atom; A represents an alkylene group having the carbon number of 2 to 4 and, when n is plural, as may be the same or different and, when different, may be random or block; Ar represents benzene wing; n represents an integer of 1 to 50.

(i-4) Examples of vinyl series monomers having a phosphoric acid group include phosphoric acid monoester of hydroxyalkyl (carbon number of 2 to 6) (meth)acrylate [for example, monophosphate of hydroxyethyl (meth)acrylate etc.], phosphoric acid diester of hydroxyalkyl (carbon number of 2 to 6) (meth)acrylate [for example, phenyl-2-acryloyloxyethyl phosphate etc.], (meth)acrylicalkyl (carbon number of 2 to 6) phosphonic acids [for example, 2-acryloyloxyethylphosphonic acid etc.] and the like.

(i-5) Examples of salts of the (i-1) to (i-4) include alkali metal salts (sodium salt, potassium salt etc.), alkaline earth metal salts (calcium salt, magnesium salt etc.), ammonium salts [ammonium, tetraalkyl(carbon number of 1 to 8)ammonium, for example, tetraoctylammonium etc.], organic amine salts {alkanolamine having the carbon number of 2 to 8, polyalkylene (carbon number of 1 to 8)polyamine(amino group number of 2 to 10) or derivatives thereof [alkylated derivatives having the carbon number of 1 to 8, alkylene oxide adduct (1 to 30 mole) having the carbon number of 2 to 12 etc.], lower alkylamine having the carbon number of 1 to 4 etc.} and the like.

(ii) Nonionic Monomers (ii-1) Examples of vinyl series monomers having a hydroxy group include monoethylenic unsaturated alcohols [for example, (meth)allyl alcohol etc.]; monoethylenic unsaturated ester or ether of 2-hydric to 6-hydric or more-hydric polyol (for example, alkylene glycol having the carbon number of 2 to 20, glycerine, polyalkylene (carbon number of 2 to 4) glycol (molecular weight of 106 to 2000) etc.) [for example, hydroxyethyl (meth)acrylate, hydroxypropyl (meth)acrylate, triethylene glycol (meth)acrylate, poly-oxyethylene-oxypropylene (random or block) glycol mono(meth)allyl ether(a hydroxy group at an end may be etherized or esterized) etc.] and the like.

(ii-2) Examples of vinyl series monomers having an amido group include (meth)acrylamide, N-alkyl(carbon number of 1 to 8) (meth)acrylamide [for example, N-methylacrylamide etc.], N,N-dialkyl(carbon number of 1 to 8)acrylamide [for example, N,N-dimethylacrylamide, N,N-di-n- or i-propylacrylamide etc.], N-hydroxyalkyl (carbon number of 1 to 8)(meth)acrylamide [for example, N-methylol(meth)acrylamide, N-hydroxyethyl(meth)akcylamide etc.]; N,N-dihydroxyalkyl(carbon number of 1 to 8)(meth)acrylamide [for examle, N,N-dihydroxyethyl (meth)acrylamide etc.], vinyllactams [for example, N-vinylpyrrolidone etc.] and the like.

(iii) Cationic Vinyl Series Monomers and Vinyl Series Monomers which Become Cationic (iii-1) Examples of vinyl series polymerizable monomers having an amino group include amino group-containing esters of monoethylenic unsaturated mono- or di-carbonic acid, for example, dialkyl(carbon number of 1 to 8)aminoalkyl(carbon number of 2 to 10) (meth)acrylate, dihydroxyalkyl(carbon number of 1 to 8)aminoalkyl(carbon number of 2 to 10) ester, morpholinoalkyl(carbon number of 1 to 8) ester and the like [for example, dimethylaminoethyl (meth)acrylate, diethylamino (meth)acrylate, morpholinoethyl (meth)acrylate, dimethylaminoethyl fumarate etc.]; amino group-containing amides of monoethylenic unsaturated mono- or di-carboxylic acid, for example, monoalkyl (carbon number of 2 to 10) (meth)acrylamide and the like [for example, dimethylaminoethyl(meth)acrylamide, diethylaminoethyl(meth)acrylamide etc.]; heterocyclic vinyl compounds [for example, vinylpyridines such as 2-vinylpyridine, 4-vinylpyridine, N-vinylpyridine and the like, N-vinylimidazole etc.]; diallylamine and the like.

(iii-2) Examples of vinyl series monomers having a quaternary ammonium group include quaternaries of tertiary amino group-containing vinyl polymerizable monomers (i.e. tertiary amino group-containing vinyl polymerizable monomers was quaternatized with a quaternarizing agent such as an alkylating agent having the carbon number of 1 to 8, for example, methyl chloride, dimethyl sulfate, benzyl chloride, dimethyl carbonate etc.), for example, trimethylaminoethyl (meth)acrylate chloride, methyldiethylaminoethyl (meth)acrylate metasulfate, trimethylaminoethyl (meth)acrylamide chloride, diethylbenzylaminoethyl (meth)acrylamide chloride and the like.

Examples of vinyl series monomers which become water-soluble by hydrolysis (a2) include vinyl series monomers having at least 1 hydrolyzable group [acid anhyride group, lower alkyl (carbon number of 1 to 3) ester group, nitrile group etc.]. Examples of vinyl series monomers having an acid anhydride group include vinyl series monomers having the carbon number of 4 to 20 of maleic anhydride, itaconic anhydride, citraconic anhydride and the like. Examples of vinyl series polymerizable monomers having an ester group include lower alkyl (C1–C3) ester of monoethylenic unsaturated carboxylic acid [for example, methyl (meth)acrylate, ethyl (meth) acrylate etc.], esters of monoethylenic unsaturated alcohol [for example, vinyl acetate, (meth)allyl acetate etc.] and the like. Examples of vinyl series monomers having a nitrile group include (meth)acrylonitrile and the like. Hydrolysis of these vinyl series monomers (a2) may be at or after polymerization and, the monomers usually form a salt and become water-soluble by hydrolysis. Examples of salts include the same salts as those described for the aforementioned salt forming group.

Among them, preferable vinyl series monomers (a) are water-soluble vinyl series monomers (a1). More preferred are vinyl series monomers having a carboxylic acid (carboxylate) group, a sulfonic acid (sulfonate) group or an amido group, and particularly preferred are (meth)acrylic acid (acrylate) and (meth)acrylamide. These vinyl series monomers (a) may be used alone or, alternatively, they may be used in combination of 2 or more of them, if necessary.

In addition, the aforementioned vinyl series monomers (a1) or (a2) together with other vinyl series monomers (a3) copolymerizable therewith may be polymerized. Examples of other polymerizable vinyl series monomers (a3) include hydrophobic vinyl series monomers, being not limited.

Examples of vinyl series monomers (a3) include the following (i) to (iv) vinyl series monomers:

(i) aromatic ethylenic monomers having the carbon number of 8–30;

styrenes such as styrene, α-methylstyrene, vinyltoluene, hydroxystyrene and the like, vinylnaphthalenes, halogenated styrenes such as dichlorostyrene and the like;

(ii) aliphatic ethylenic monomers having the carbon number of 2 to 20;

alkenes [ethylene, propylene, butene, isobutylene, pentene, heptene, diisobutylene, octene, dodecene, octadecene etc.]; alkadienes [butadiene, isoprene etc.] and the like;

(iii) alicyclic ethylenic monomers having the carbon number of 5 to 15;

monoethylenic unsaturated monomers [pinene, limonene, indene etc.]; polyethylenic vinyl polymerizable monomers [cyclopentadiene, bicyclopentadiene, ethylidenenorbornene etc.] and the like;

(iv) (meth)acrylic acid esters having an alkyl group having the carbon number of 4 to 50;

n-butyl (meth)acrylate, 2-ethylhexyl (meth)acrylate, dodecyl (meth)acrylate, hexadecyl (meth)acrylate, heptadecyl (meth)acrylate, eicosyl (meth)acrylate and the like;

An amount of a vinyl series monomer (a3) is preferably 0 to 50% by weight, more preferably 0 to 25% by weight relative to a vinyl series monomer (a).

In the present invention, examples of a cross-linking agent (b) include a first cross-linking agent (b1) which is used at polymerization of a vinyl series monomer (a) and a surface cross-linking agent (second cross-linking agent) (b2) which cross-links the surface of a particle obtained by drying and pulverizing after polymerization. Examples of the first cross-linking agent (b1) include cross-linking agents having 2 or more ethylenic unsaturated groups, cross-linking agents having at, least 1 functional group reactive with a functional group of a vinyl series monomer (a) and at least 1 ethylenic unsaturated group, and cross-linking agents having at least 2 functional groups reactive with a functional group of a vinyl series monomer (a).

(i) Examples of cross-linking agents having 2 or more ethylenic unsaturated groups include N,N'-methylenebis(meth)acrylamide, ethylene glycol di(meth)acrylate, polyethylene glycol di(meth)acrylate, propylene glycol di(meth)acrylate, glycerin (di or tri)acrylate, trimethylolpropenetriacrylate, triallylamine, triallyl cyanurate, triallyl isocyanurate, tetraaryloxyethane, pentaerythritol triallyl ether and the like.

(ii) Examples of cross-linking agents having at least 1 functional group reactive with a functional group (for example, carboxyl group) of a vinyl series monomer (a) and at least 1 ethylenic unsaturated group include cross-linking agents having at least 1 functional group reactive with carboxylic acid (carboxylate) group, hydroxyl group, amino group or the like and at least 1 ethylenic unsaturated group, such as ethylenic unsaturated group having epoxy group such as glycidyl (meth)acrylate, N-methylol(metha)acrylamide and ethylenic unsaturated group having hydroxy group such as hydroxyethyl (meth)acrylate.

(iii) Examples of cross-linking agents having at least 2 functional groups reactive with a functional group of vinyl series monomers (a) include cross-linking agents having at least 2 functional groups reactive with carboxylic acid (carboxylate) group, hydroxyl group, amino group or the like, for example, polyglycidyl ether compounds having 2 to 10 epoxy groups in one molecule [ethylene glycol diglycidyl ether, glycerin-1,3-diglycidyl ether, glycerin triglycidyl ether, polyethylen glycol (degree of polymerization of 2 to 100) diglycidyl ether, polyglycerol (degree of polymerization of 2 to 100) polyglycidyl ether etc.]; 2-hydric to 20-hydric polyol compounds [glycerin, ethylene glycol, polyethylene glycol,(degree of polymerization of 2 to 100) etc.]; 2-hydric to 20-hydric polyamine compounds (ethylenediamine, diethylentriamine etc.); polyamine series resins having a molecular weight of 200 to 500,000 (polyamidepolyamineepichlorohydrin resin, polyamineepichlorohydrin resin etc.), alkylene carbonate [ethylene carbonate etc.], aziridine compounds, polyimine compound and the like. These cross-linking agents may be used alone or in combination of 2 or more of them.

An amount of the first cross-linking agent (b1) to be used is preferably 0.001 to 5.0% by weight, more preferably 0.002 to 2% by weight, particularly preferably 0.003 to 1.6% by weight based on a weight of the vinyl series monomers (a) or a total weight of the vinyl series monomers (a) and the vinyl series monomers (a3). When the amount of the first cross-linking agent (b1) is 0.001% by weight or more, the water retaining capacity and the absorbing capacity are better. When the amount is 5.0% by weight or less, the cross-linking does not become too strong and the water retaining capacity and the absorbing capacity are not lowered.

A method for polymerizing a cross-linked polymer (A) in the present invention in not particularly limited as long as the cross-linked polymer (A) exhibits the above respective properties. There are the previously known methods, for example, a solution polymerizing method, an emulsion polymerizing method, a suspension polymerizing method, a reverse phase suspension polymerizing method, a film polymerizing method, a spray polymerizing method and the like using an initiator. As a method for controlling polymerization, there are an adiabatic polymerizing methods, a temperature controlled polymerizing method, an isothermal polymerizing method and the like. When the suspension polymerizing method or reverse phase suspension polymerizing method is used as a polymerizing method, polymerization is performed in the presence of the previously known dispersant, protective colloid or surfactant, or a mixture of 2 or more of them, if needed. In the case of the reverse phase suspension polymerizing method, polymerization is performed using the previously known solvent such as cyclohexane, n-hexane, n-heptane, xylene and the like. Preferably, the solution polymerizing method using an initiator is used. Particularly preferably, an aqueous solution polymerizing method is used because it is not necessary to use an organic solvent and it is advantageous in respect of the production cost.

The polymerization initiator (c) is not particularly limited but the previously known initiators can be used as long as they are an azo series initiator, a peroxide series initiator, a redox initiator or an organic halogenated initiator. Examples thereof are as follows:

(i) Examples of the azo series initiator include azobisisobutyronitrile, azobiscyanovaleric acid and salts thereof, 2,2'-azobis(2-amidinopropane) hydrochloride, 2,2'-azobis(2-methyl-N-(2-hydroxyethyl)propionamide and the like.

(ii) Examples of the peroxide initiator include inorganic peroxides [hydrogen peroxide, ammonium persulfate, potassium persulfate, sodium persulfate etc.], organic peroxides [benzoyl peroxide, di-t-butyl peroxide, cumenehydroperoxide, succinicperoxide, di(2-ethoxyethyl)peroxydicarbonate etc.]

(iii) Examples of the redox series initiator include a combination of a reducing agent such as sulfite or bisulfite of alkali metals, ammonium sulfite, ammonium bisulfite, ferric chloride, ferric sulfate, ascorbic acid and the like and an oxidizing agent such as persulfate of alkali metals, ammonium persulfate, hydrogen peroxide, organic peroxide and the like.

(iv) Examples of halogen of an organic haloganated compounds initiator include fluorine, chlorine, bromine and iodine.

Examples of the organic haloganated compounds are not particularly limited but, from a viewpoint of polymerizability, include preferably organic haloganated compounds having the halogen number of 1 to 10 or more and the carbon number of 1 to 15 or more selected from the group consisting of haloganated alkyl, haloganated alkyl phenyl ketone, haloganated alkylcarboxylic acid and haloganated alkylcarboxylic acid alkylester. More preferably, examples include tetrachloromethane, trichlorobromomethane, trichloroiodomethane, dichloromethyl phenyl ketone, 1-bromo-1-mehtylethylcarboxylic acid, and 1-bromo-1-methylethylcarboxylic acid alkylester having an alkyl group of the carbon number of 1 to 8 (for example, methyl 1-bromo-1-methylethylcarboxylate, ethyl 1-bromo-1-methylethylcarboxylate, octyl 1-bromo-1-methylethylcarboxylate and lauryl 1-bromo-1-methylethylcarboxylate). Particularly preferably, examples include dichloromethyl phenyl ketone, and 1-bromo-1-methylethylcarboxylic acid alkylester having an alkyl group of the carbon number of 1 to 8.

These initiators may be used alone or in combination of 2 or more of them. Preferably, the azo series initiator, the redox series initiator and a combination thereof are used.

An amount of the polymerization initiator (c) is preferably 0.005 to 0.5% by weight, more preferably 0.007 to 0.4% by weight, particularly preferably 0.009 to 0.3% by weight based on a total weight of the vinyl series monomer (a) and the cross-linking agent (b) or a total weight of the vinyl series monomer (a), the vinyl series monomer (a3) and the cross-linking agent (b).

In order that the present cross-linked polymer (A) exhibits the aforementioned respective properties, the cross-linked polymer (A) must be highly polymerized. For that, for example, the cross-linked polymer (A) can be obtained by either of the following methods ① to ③. These methods may be combined.

① Polymerization is performed so that the concentration of a total amount of the vinyl series monomer (a) and the cross-linking agent (b) or a total amount of the vinyl series monomer (a), the vinyl series monomer (a3) and the cross-linking agent (b)(whole vinyl series monomer) in a polymerization solution is 20% by weight or less.

② Preferably 70% by weight or more, more preferably 80% by weight or more of the whole vinyl series monomer in a polymerization solution is polymerized at a polymerization temperature of 60° C. or lower and at a constant temperature with a temperature controlled width of preferably ±5° C., more preferably ±2° C. Almost all of, that is, 70% by weight of the whole vinyl series monomer is constant temperature-polymerized at a temperature of 60° C. or lower.

③ Polymerization is performed in the presence of a complex compound (d) of a metal element (d1) and a ligand (d2) of an anion or a neutral molecule.

As the present cross-linked polymer (A), the cross-linked polymer by ③ is particularly preferable.

The complex compound (d) is a complex compound of a metal element (d1) and a ligand (d2) of an anion or a neutral molecule, and has the structure in which the metal element (d1) is surrounded by a ligand (d2) of an anion or a neutral molecule.

The metal element (d1) is not particularly limited as long as it is a metal element. Examples thereof include main group element metals, for example, IA group element metals (lithium, sodium, potassium, cesium etc.), IB group element metals (copper, silver, gold etc.), IIA group element metals (magnesium, calcium, barium etc.), IIIA group element metals (scandium, yttrium), IIIB group element metals (aluminium, gallium, indium, thallium etc.), IVA group element metals (titanium, zirconium, hafnium), IVB group element metals (tin, zinc etc.), VA group element metals (vanadium, niobium, tantalum), VB group element metals (antimony, bismuth etc.), VIA group element metals (chromium, molybdenum, tungsten), VIB group element metals (tellurium, polonium etc.), VIIA group element metals (manganese, technetium, rhenium), VIII group element metals (iron, cobalt, nickel, ruthenium, rhodium, palladium, osmium, iridium, platinum), lanthanide group element metals (lanthanum, cerium etc.), actinoid group element metal (actinium, thorium etc.) and the like. From a viewpoint of polymerizability of a vinyl polymerizalble monomer, IB group, IIIA group, IVA group, VA group, VIA group, VIIA group, VIII group and lanthanoid group element metals are preferable, IB group, VIII group and lanthanide group element metals are more preferable, and IB group, and 4–6 Period VIII group element metals are particularly preferable. From a viewpoint of easy handling and workability, 5 Period VIII group element metals (ruthenium, rhodium, palladium) are most preferable.

The metal element (d1) is usually present as a cation but may be neutral as pentacarbonyliron in addition to a cation.

A ligand (d2) of an anion or a neutral molecule is not particularly limited as long as it is a ligand which is an anion or a neutral molecule. Examples thereof include ① an anion of an atom selected from hydrogen and halogen, ② a compound having 1 or 2 or more atoms selected from nitrogen, oxygen, phosphorus and sulfur, and ③ 1 or 2 or more selected from conjugated system compounds.

More particularly, examples are as follows:

Examples of:

① an anion of an atom selected from hydrogen and halogen; an anion of hydrogen, fluorine, chlorine, bromine and iodine;

② a compound having 1 or more atoms selected from the group consisting of nitrogen, oxygen, phosphorus and sulfur; are as follows. Preferred are compounds having a molecular weight of 1,000 or less (those that can coordinate at 2 or more places are classified into either of coordinatable groups).

(1) Tertiary phosphine compounds having the phosphorus number of 1 to 4 or more and the carbon number of 3 to 42;

trimethylphosphine, triethylphosphine, diethylphenylphosphine, triphenylphosphine (hereinafter, abbreviated as PPh3), ortho-phenylenebis (diphenylphosphine), ortho-phenylenebis (dimethylphosphine), ortho-phenylenebis (diethylphosphine), ortho-phenylenebis (ethylphenylphosphine), 1,2-bis(diphenylphosphino)ethane, 1,2-bis(dimethylphosphino)ethane (hereinafter, abbreviated as dppe), 1,2-bis(diethylphosphino)ethane, 1,2-bis (ethylphenylphosphino)ethane, 1,2-bis(diphenylphosphino) methane (hereinafter, abbreviated as dppm), 1,2-bis (dimethylphosphino)methane, 1,2-bis(diethylphosphino) methane, 1,2-bis(ethylphenylphosphino)methane, tris (diphenylphosphinoethyl)phosphine, tris (diethylphosphinoethyl)phosphine, tris (dimethylphosphinoethyl)phosphine, tris (ethylphenylphosphinoethyl)phosphine and the like;

(2) ammonium or amines having the nitrogen number of 1 to 4 or more and the carbon number of 0 to 44 or more;

(2-1) nitrogen number 1; pyridine (hereinafter, abbreviated as py), diethylamine, salicylamine, aminoethaneselenol, 2-hydroxy-6-methylpyridine, 2-diethylaminoethanol, bis(2-aminoethyl)amide, ethanolamine, 2-aminoethanol, β-alanine, 2-hydroxy-6-methylpyridine, 3-salicylideneamino-1-propanol, 2-pyrrolidone, 8-quinolinol, salicylaldimine, α-picoline and the like;

(2—2) nitrogen number 2; ethylenediamine (hereinafter, abbreviated as en), propylenediamine, trimethylenediamine, 1,2-cyclohexanediamine, N,N-diethylethylenediamine, N,N-dimethylethylenediamine, salicylideneethylenediamine, N-ethylsalicylaldiamine, bis (benzoylacetone)ethylenediamine 1,2-diamino-1,1'-dimethylethane, 2,2'-bipyridine (hereinafter, abbreviated as bpy), 2,2'-bipyridine (hereinafter, abbreviated as bpy), 2,2'-bipyridine-3-yne, 2,2'-bipyridine-N,N'-dioxide, dicyandiamidine, (aminoiminomethyl)urea, [(2-aminoethyl) amino)]-1-propanol, 2-[(3-aminopropyl)amino]ethanol, N-2-[2-(diethylamino)ethyl]-3-amino-1-propanol, tris[2-(methylamino)ethyl]amine, imidazole, N,N'-disalicylidenetrimethylenediamine, 4,6,6-trimethyl-3,7-diazanona-3-ene-1,9-diol, N,N,N',N'-tetramethylethylenediamine, 1,8-naphthyridine and the like;

(2-3) nitrogen number 3 or more; diethylenetriamine, triethylenetetramine, tetraethylpentamine, N,N'-bis(2-aminobenzylidene)ethylenediamine, tris[2-(methylamino) ethyl]amineaminopyridine, 1,3-bis [bis(2-pyridylethyl) aminomethyl]benzene, 4-dimethylamino-2,3-dimethyl-1-phenyl-5-pyrazolone, biguanide, imidodicarbonimidodiamide, biuret, carbamoylguanidine, phthalocyanine, N,N,N',N'-tetrakis(2-aminoethyl) ethylenediamine, 1,2,3-triaminopropane, tris(2-benzimidazolylmethyl)amine, tetrakis(2-pyridylmethyl) ethylenediamine, 2,2',2"-terpyridine, 1,4,7,10-tetraazadecane, 1,4,8,11-tetraazaundecane, 1,5,8,12-tetraazadodecane, 1,4,8,11-tetraazacyclotetradecane, ethylenebis(biguanide), tetraphenylporphyrin, tris(2-pyridylmethyl)amine, histidine and the like;

(3) carbonyl group-containing compounds (except for carboxylic acid) having the carbonyl group of 1 to 3 or more and the carbon number of 3 to 40 or more;
ethyl acetoacetate, acetylacetone (hereinafter, abbreviated as acac), 2,4-pentanedione, bis(acetylacetone), 3-methylpentane-2,4-dione, 1-phenyl-1,3-butanedione, 3-phenylpentane-2,4-dione, 1,3-diphenyl-1,3-propanedione, 1-phenyl-1,3,5-hexanetrione, 5,5'-(1,2-ethanediyldinitrilo) bis(1-phenyl-1,3-hexanedione), trifluoroacetylacetone, hexafluoroacetylacetone, benzyl, dibenzoylmethane, asparaginebenzoylacetone, thenoyltrifluoroacetone, 4,4'-(1,2-ethanediyldinitrilo)bis(2-pentanone), dipivaloylmethane and the like;

(4) carboxylic acids having the carboxylic acid number of 1 to 4 or more and the carbon number of 2 to 20 or more;
oxalic acid, malonic acid, salicylic acid, phthalic acid, nicotinic acid, picolinic acid, aspartic acid, benzoylpyruvic acid, ethylenediamine diacetic acid, nitrilotriacetic acid, N'-(2-hydroxyethyl)ethylenediaminetriacetic acid, propylenediaminetetraacetic acid, ethylenediaminetetraacetic acid, trans-1,2-cyclohexanediaminetetraacetic acid, trans-1, 2-(cyclohexanedinitrilo)tetraacetic acid, (1,2-ethanediyldinitrilo)tetraacetic acid, ethylenediaminetetrapropionic acid, glycine, N-methylglycine, glycylglycine, glycylglycylglycylglycine, salicylideneglycine, iminodiacid, methyliminodiacetic acid, N,N-diethyldiselenocarbamic acid, methionine, proline, sarcosine, xanthic acid and the like;

(5) oximes having the oxime number of 1 to 4 or more and the carbon number of 2 to 20 or more;
dimethylglyoxime, 3-(2-aminoethylimino)-2-butanoneoxime, benzylmethylglyoxime, 2,6-diacetylpyridinedioxime, 2-pyridylaldoxime, 3-phenylimino-2-butanoneoxime, salicylaldehydeoxime and the like;

(6) phenols having the phenol number of 1 to 4 or more and the carbon number of 6 to 30 or more;
catechol, 1,2-benzenediol, 1,3-bis[bis(2-pyridylethyl) aminomethyl]phenol, 2,6-bis[bis(2-pyridylethyl) aminomethyl]-4-phenol, 1-nitroso-2-naphthol and the like;

(7) ethers having the ether number of 1 to 8 or more and the carbon number of 4 to 30 or more;
tetrahydrofuran, 1,4-dioxane, tetrahydrofuran, 1,4,7,10-tetraoxacyclotetradecane, 1,4,7,10,13-pentaoxacyclopentadecane, 1,4,7,10,13,16-hexaoxycyclooctadecane, 4,7,13,16-tetraoxa-1,10-diazacyclooctadecane, 4,7,13,18-tetraoxa-1,10-diazabicyclo [8,5,5,]icosane, 2,3-benzo-1,4,7,10,13-pentaoxacyclopentade-2-cene, 4,7,13,16,21-pentaoxa-1,10-diazabicyclo[8,5,5,]tricosane, monensin, nigeridine and the like;

(8) sulfur compounds having the sulfur number of 1 to 4 or more and the carbon number of 2 to 40 or more;
diethyldithiocarbamic acid, ethylthioglycolic acid, ethylenebisthioglycolic acid, ethylenethiourea, phenyldithioacetic acid, dithiobenzoic acid, 1,2-aminoethanethiol, diphenylthiocarbazone, dimethyl sulfoxide, 2,4-pentanedithione, 2,2,7,7-tetramethyl-3,6-dithiaoctane, 2-imidazolidinethione, dimethyldithiocarbamic acid, thiourea, cysteine, maleonitriledithiol, 1,4,8,11-tetrathiaundecane and the like;

(9) amide compounds having the amide group number of 1 to 3 or more and the carbon number of 3 to 54 or more;
diazoamide, N,N-dimethylacetamide, N,N-dimethylformamide, hexamethylphosphoric triamide, diphenylphosphinic amide, aminoethylamide, oxamide, valinomycin, phthalimide, succinimide, valinomycin and the like;

(10) N-oxides having the N-oxide group number of 1 to 3 or more and the carbon number of 6 to 20 or more;
α-picoline-N-oxide, γ-picoline-N-oxide, pyridine-N-oxide and the like;

(11) others;
nitrogen molecule, water, carbon monoxide, urea, salicylaldehyde, N-nitrosophenylhydroxylaminic acid hydrogen and the like; and the like.

③ Examples of the conjugated system compounds having the unsaturated group number of 2 to 10 or more and the carbon number of 4 to 14 or more are as follows:
1,5-cyclooctanediene (hereinafter, referred to as cod), 1,3,5,7-cyclooctatetraene, cyclopentadienyl, pentamethylcyclopentadienyl, tropolone, 1,10-phenanthroline and the like;

From a viewpoint of vinyl polymerizability, preferred are halogen (fluorine, chlorine, bromine and iodine) ions and phosphorus-containing compounds, and particularly preferred are an anion of an atom selected from chlorine, bromine and iodine and tertiary phosphine compounds.

The complex compound (d) can be usually synthesized by mixing a salt of a metal element (d1) (for example, a haloid of a metal etc.) and a ligand (d2) of an anion or a neutral molecule at room temperature. Alternatively, after other intermediate complex compound is formed, an end complex compound is made in some cases. The salt of a metal element (d1) and a ligand (d2) of an anion or a neutral molecule may be mixed as it is or after dissolved in an aqueous solution/solvent solution, or may be mixed in an aqueous solution/solvent solution. If needed, it may be heated to 30 to 200° C. When a substance to be removed is produced, it can be removed under reduced pressure. The produced complex compound (d) may be taken out as it is or as crystals, and may be used by purification. Examples of solvent used herein include alcohol series solvents (methanol, ethanol etc.), ketone series solvents (acetone, methyl ethyl ketone etc.), amide series solvents (N,N-dimethylformamide, N-methylpyrrolidone etc.), sulfoxide series solvents (dimethyl sulfoxide etc.), and a mixture of 2 or more of them.

There are so many complex compounds (d) and individual methods for synthesis are described, for example, in Angew. Chem. Int. Ed. Engl., 12,57(1973); J. Chem. Educ., 50,343 (1973); Accts. Chem. Research, 3, 105(1970); Chem. Rev., 73,487(1973); Interscience-Wilry(1968); Chem. Soc. Rev., 4,27(1975); Fundamental Inorganic Chemistry (co-authored by F. A. Cotton and G. Wirylkinson, Baifukan); dictionary for inorganic compounds and complexes (Katsuyoshi Nakahara, Kodansha).

Examples of the form of coordination are not particularly limited but include monodentate coordination (an example of a ligand is triphenylphosphine), didentate coordination (an example of a ligand is ethylenediamine), and polydentate (tri-hexa-dentate) (an example of a ligand is terpyridine). Usually, the complex compound takes the form of coordination of a combination of them. The complex compound (d) is usually a non-electrolytic complex compound having no charge but may be an electroltic complex compound such as a complex cation, a complex anion and the like having charge.

Examples of the complex compound (d) are as follows:
(1) In the case where the metal element (d1) is a IB group metal element
    [Cu(CH$_3$)(PPh$_3$)], [Cu$_2$Cl(cod)$_2$], [Ag(py)$_2$]Cl, [Ag(py)$_4$]Cl, [Ag(py)$_4$]Cl$_2$, [AuCl(PPh$_3$)], [AuCl$_3$(PPh$_3$)], [Au(dppe)]Cl etc.;
(2) In the case where (d1) is the Fourth Period VIII group metal element
    [FeCl$_2$(bpy)$_2$], [FeCl$_2$(bpy)$_2$]Cl, [FeCl(H)(CO)(PPh$_3$)$_3$], [FeCl(H)(dppe)$_2$], [FeCl$_3$(NO)(PPh$_3$)$_2$], [FeCl$_2$(PPh$_3$)$_3$], [FeCl$_2$(PPh$_3$)$_4$], [Fe(CN)$_2$(bpy)2], [Fe(CO)$_2$(PPh$_3$)$_3$], [Fe(H)$_2$(N$_2$)(PPh$_3$)$_3$], [Co$_2$Cl$_2$(cod)$_2$], [CoCl(CO)(PPh$_3$)$_2$], [CoCl(PPh$_3$)$_3$], [CoCl(O$_2$)(PPh$_3$)$_3$], [COCl$_3$(py)$_3$], [Co(cod)$_2$Cl, [Co(H)(CO)(PPh$_3$)$_3$], [Ni(acac)Cl(PPh$_3$)], [NiBr(CH$_3$){P(C$_2$H$_5$)$_3$}$_2$], [NiBr(NH$_3$)$_3$], [Ni(CH$_3$)Cl(cod)], [Ni(C$_2$H$_5$)(cod)]Cl, [Ni(CH$_3$)(PPh$_3$)], [Ni$_2$Cl$_2$(acac)$_2$], [NiCl$_2$(bpy)], [NiCl$_2$(cod)], [Ni$_2$Cl$_2$(dppm)], [NiCl$_2$(en)], [NiCl$_2$(NH$_3$)(PPh$_3$)], [NiCl$_2$(PPh$_3$)], [Ni$_2$Cl$_4$(PPh$_3$)$_2$], [Ni(PPh$_3$)$_4$], [Ni(py)$_4$]Cl$_2$, [Ni(SO$_3$)(H$_2$O)$_3$], [Ni(SO$_3$)(NH$_3$)$_3$]etc;
(3) In the case where the metal element (d1) is The Fifth Period VIII group metal element
    [Rh$_2$Cl$_2$(cod)$_2$], [RhCl(CO)(PPh$_3$)$_2$], [RhCl(PPh$_3$)$_3$], [RhCl(O$_2$)(PPh$_3$)$_3$], [RhCl$_3$(py)$_3$], [Rh(cod)$_2$]Cl, [Rh(H)(CO)(PPh$_3$)$_3$], [RuCl$_2$(bpy)$_2$], [RuCl$_2$(bpy)$_2$]Cl, [RuCl(H)(CO)(PPh$_3$)$_3$], [RuCl(H)(dppe)$_2$], [RuCl$_3$(NO)(PPh$_3$)$_2$], [RuCl$_2$(PPh$_3$)$_3$], (RuCl$_2$(PPh$_3$)$_4$], [Ru(CN)$_2$(bpy)2], [Ru(CO)$_2$(PPh$_3$)$_3$], [Ru(H)$_2$(N$_2$)(PPh$_3$)$_3$], [Pd(acac)Cl(PPh$_3$)], [PdBr(CH$_3$) {P(C$_2$H$_5$)$_3$}$_2$], [PdBr(NH$_3$)$_3$], [Pd(CH$_3$)Cl(cod)]], [Pd(C$_2$H$_5$)(cod)]Cl, [Pd(CH$_3$)(PPh$_3$)], [Pd$_2$Cl$_2$(acac)$_2$], [PdCl$_2$(bpy)], [PdCl$_2$(cod)], [Pd$_2$Cl$_2$(dppm)], [PdCl$_2$(en)], [PdCl$_2$(NH$_3$)(PPh$_3$)], [PdCl$_2$(PPh$_3$)], [Pd$_2$Cl$_4$(PPh$_3$)$_2$], [Pd(PPh$_3$)$_4$], [Pd(py)$_4$]Cl$_2$, [Pd(SO$_3$)(H$_2$O)$_3$], [Pd(SO$_3$)(NH$_3$)$_3$] etc.;
(4) In the case where the metal element (d1) is the Sixth Period VIII group metal element
    [OsCl$_2$(bpy)$_2$], [OsCl$_2$(bpy)$_2$]Cl, [OsCl(H)(CO)(PPh$_3$)$_3$], [OsCl(H)(dppe)$_2$], [OsCl$_3$(NO)(PPh$_3$)$_2$], [OsCl$_2$(PPh$_3$)$_3$], [OsCl$_2$(PPh$_3$)$_4$], [Os(CN)$_2$(bpy)$_2$], [Os(CO)$_2$(PPh$_3$)$_3$], [Os(H)$_2$(N$_2$)(PPh$_3$)$_3$], [Ir$_2$Cl$_2$(cod)$_2$], [IrCl(CO)(PPh$_3$)$_3$], [IrCl(PPh$_3$)$_3$], [IrCl(O$_2$)(PPh$_3$)$_3$], [IrCl$_3$(py)$_3$], [Ir(cod)$_2$]Cl, [Ir(H)(CO)(PPh$_3$)$_3$], [Pt(acac)Cl(PPh$_3$)], [PtBr(CH$_3$){P(C$_2$H$_5$)$_3$}$_2$], [PtBr(NH$_3$)$_3$], [Pt(CH$_3$)Cl(cod)], [Pt(C$_2$H$_5$)(cod)]Cl, [Pt(CH$_3$)(PPh$_3$)], [Pt$_2$Cl$_2$(acaC)$_2$], [PtCl$_2$(bpy)], [PtCl$_2$(cod)], [Pt$_2$Cl$_2$(dppm)], [PtCl$_2$(en)], [PtCl$_2$(NH$_3$)(PPh$_3$)], [PtCl$_2$(PPh$_3$)], [Pt$_2$Cl$_4$(PPh$_3$)$_2$], [Pt(PPh$_3$)$_4$], [Pt(py)$_4$]Cl$_2$, [Pt(SO$_3$)(H$_2$O)$_3$], [Pt(SO$_3$)(NH$_3$)$_3$] etc.

The complex compound is not particularly limited and the compounds in the aforementioned range can be applied.

Preferred are complex compounds having the Fifth Period VIII group metal element (ruthenium, rhodium, palladium) and a ligand selected from the group consisting of an anion of an atom selected from chlorine, bromine and iodine, and a tertiary phosphine compound, such as [RuCl$_2$(PPh$_3$)$_3$], [RuCl$_2$(PPh$_3$)$_4$], [Pd$_2$Cl$_2$(dppm)], [RhCl(CO)(PPh$_3$)$_2$], [RhCl(PPh$_3$)$_3$] etc.

It is preferable from a viewpoint of the polymerizability and operability that a complex compound (d) is a complex compound which dissolves in water or a water-soluble organic solvent. Examples of the water-soluble organic solvent include the same water-soluble organic solvents as those used for synthesis of the complex compound (d).

Preferably, an amount of a complex compound (d) is 0.005 ppm to 2% by weight and an amount of a metal element (d1) is 0.001 ppm to 1% by weight and, more preferably, an amount of a complex compound (d) is 0.01 ppm to 1% by weight and an amount of a metal element (d1) is 0.005 ppm to 0.5% by weight and, particularly preferably, an amount of a complex compound (d) is 0.02 ppm to 0.6% by weight and an amount of a metal element (d1) is 0.01 ppm to 0.3% by weight based on the weight of the vinyl series monomer (a) and the cross-linking agent (b) or a total weight of the vinyl series monomer (a), the vinyl series monomer (a3) and the cross-linking agent (b).

When an amount of the complex compound (d) is 0.005 ppm to 2% by weight and an amount of (d1) is 0.001 ppm to 1% by weight, the performance as an absorbing article is exhibited and, at the same time, a polymerization rate and a proportion of polymerization of the vinyl series monomer becomes sufficient, leading to the better productivity.

When the solubility of the complex compound (d) in an aqueous polymerization solution is low, polymerization may be performed by dissolving or dispersing the complex compound in an aqueous polymerization solution of the aforementioned vinyl series monomer (a) using a water-soluble organic solvent, a surfactant and the like.

In the present invention, it is preferable that 1 or more vinyl series monomers (a) which are water-soluble and/or become water-soluble by hydrolysis are vinyl-polymerized in the presence of water. The polymerization concentration, that is, the concentration of the whole vinyl series monomer

[a total weight of the vinyl series monomers (a) and (b) or a total weight of the vinyl series monomer (a), vinyl series monomers (a3) and (b) (whole vinyl series monomer)] in a polymerization solution is preferably 10 to 45% by weight, more preferably 12 to 40% by weight, particularly preferably 15 to 35% by weight based on a total weight of the polymerization solution. When the concentration of the whole vinyl series monomer is 10% by weight or more, it is the sufficient concentration for the use of after polymerization, being effective. On the other hand, the concentration is 45% by weight or less, a molecular weight of a polymer obtained in the case of use of the complex compound (d) does not become low, side reactions such as self cross-linking and the like do not occur and, whereby, a molecular weight distribution of a main chain becomes narrow, and the resulting polymer can manifest the aforementioned respective properties such as water retaining amount, absorbing amount under load and the like. It is preferable that an amount of water is 90 to 55% by weight relative to the whole. When an amount of water is 90% by weight or less, it is the sufficient concentration for use after polymeraization, being effective. When the amount is 55% by weight or more, a molecular weight of the resulting polymer main chain is not lowered, side reactions such as self cross-linking and the like do not occur, a molecular weight distribution becomes narrow and, thus, it becomes possible to manifest respective properties of the present invention.

In polymerization of the present vinyl series monomer (a) and cross-linking agent (b), other polymerization conditions such as a polymerization temperature, time and the like are not particularly limited as long as they can manifest the present respective properties. The known conditions may be used, for example, a polymerization initiation temperature may be variously changed depending upon a kind of a polymerization initiator and is usually −5° C. to 90° C., preferably 2° C. to 70° C. In addition, a chain transfer agent (for example, isopropanol, thiol series chain transfer agent, sodium hypophosphite etc.) may be added.

Alternatively, polymerization may be performed in the presence of a graft substrate. Examples of this graft substrate include natural sugars such as starch and cellulose or the natural modified sugars thereof, and water-soluble or water-dispersible synthetic resins such as polyalkylene oxide, polyvinyl alcohol, poly(meth)acrylate, polyester and the like.

The resulting cross-linked polymer may be kneaded with the aforementioned cross-linking agent (iii) or a multivalent metal compounds (calcium chloride, magnesium sulfate, aluminium sulfate etc.) and the like which can form an ion bridge in the state of a hydrate gel, and may be further cross-linked, if needed. This leads to comparatively uniform cross-linking and, a cross-linked polymer having the high gel strength and small water-soluble component amount can be prepared.

A hydrate gel-like polymer of the cross-linked polymer thus obtained is dried, ground, and a part near the surface of the cross-linked polymer obtained by further adjusting particle size, if necessary, is surface-cross-linked with a cross-linking agent (second cross-linking agent) to obtain a cross-linked copolymer (A), which can further improve the excellent capacity as the present absorbing article.

As a method for drying, there are the conventional method such as a method of drying with a hot air at a temperature of 80 to 230° C., a film drying method using a drum drier heated at 100° C. to 230° C., a (heating) reduced pressure drying method, a freezing drying method, a method of drying with the infrared ray and the like.

A grinding method is not particularly limited but the conventional apparatuses such as a hammer type grinding machine, an impact type grinding machine, a roll type grinding machine and a jet air stream type grinding machine are used. The resulting ground material is classified to adjust a particle size by sieve, if necessary. The shape of a cross-linked polymer after grinding is not particularly limited but examples thereof include indefinite ground-like, flake-like, pearl-like, rice grain-like, granule-like and the like. The indefinite ground-like is preferable in that it is well entangled with a fibrous material for use in a diaper, and there is no peeling from a fibrous material.

A weight average particle size of the resulting cross-linked polymer is preferably 100 to 800 μm, more preferably 200 to 500 μm. The cross-linked polymer which has been ground so that 95% by weight or more of particles are in a range of 100 to 850 μm can be used. The smaller content of fine particles is preferable. Preferably, the content of particles of 100 μm or smaller is 3% or less and, more preferably, the content of particles of 150 μm is 3% or less. A weight average particle size is obtained by plotting each particle size distribution of an absorbing resin on a logarithmic probability paper in which a transverse axis is a particle size and an ordinate axis is the content by weight, and obtaining a particle size at which 50% of a total weight is occupied.

As a method of surface-cross-linking this cross-linked polymer, there are the previously known methods, for example, a method of mixing a mixed solution of a second cross-linking agent (b2), water and an organic solvent with this cross-linked polymer, which is heated to react.

The second cross-linking agent (b2) may be the same as or different from the aforementioned first cross-linking agent (b1) and is preferably a cross-linking agent having at least 2 functional groups reactive with an acid group such as (iii) carboxyl group and the like, and/or its base. Particularly preferable, the second cross-linking agent is a polyglycidyl ether compound, a polyamine series resin and an aziridine compound in that surface cross-linking can be performed at a relatively low temperature.

An amount of a second cross-linking agent (b2) to be used is preferably 0.001 to 7.0% by weight, more preferably 0.002 to 5.0% by weight, particularly preferably 0.003 to 4.0% by weight based on the weight of the vinyl series monomer (a) or a total weight of the vinyl series monomer (a) and the vinyl series monomer (a3). When the amount of the second cross-linking agent (b2) to be used is 0.001% by weight or more, a degree of surface cross-linking is sufficient, and the effects of improving absorbing amount under load become sufficient. On the other hand, the amount of a second cross-linking agent (b2) to be used is 7.0% by weight or less, a cross-linking degree of the surface does not become excessive and an water retaining amount is not lowered.

An amount of water to be used at surface cross-linking is preferably 1 to 10%, more preferably 2 to 7% based on the weight of a cross-linked polymer. When the amount of water to be used is 1% or more, penetration of a second cross-linking agent (b2) into the interior of a particle of a cross-linked polymer becomes sufficient, the effects of improving absorbing amount under load, in particular absorbing amount under particularly high load (for example, 60 g/cm$^2$) becomes better. On the other hand, an amount of water to be used is 10% or lower, penetration of a second cross-linking agent (b2) into the interior of a cross-linked polymer does not become excessive, improvement in absorbing amount under load is recognized, there arises no problem that a water retaining amount is considerably lowered.

In the present invention, as an organic solvent to be used together with water, the previously known hydrophilic solvents can be used and appropriately selected taking into consideration a degree of penetration into the interior of a cross-liked polymer of a second cross-linking agent (b2), the reactivity of the second cross-linking agent (b2) and the like. Preferred are hydrophilic organic solvents which can be dissolved in water, such as methanol, diethylene glycol and the like. Such the solvents may be used alone, or as a combination of 2 or more of them.

An amount of a solvent can vary depending upon a kind of the solvent, and is preferably 1 to 10% based on the weight of a cross-linked polymer. In addition, the amount can vary arbitrarily depending upon a ratio of the solvent relative to water and is preferably 20 to 80%, more preferably 30 to 70% in terms of weight.

A mixed solution of the second cross-linking agent (b2), water and the solvent is added to the cross-linked polymer to mix them according to the previously known method, and a reaction is performed while heating. A reaction temperature is preferably 80 to 200° C., more preferably 100 to 160° C. A reaction time can vary preferably 5 to 40 minutes.

The particulate cross-linked polymer (A) obtained by such the surface cross-linking may be additionally surface-cross-linked with the same kind of second cross-linking agent (b2) or a different kind of a second cross-linking agent (b2) from that used for (A).

The particulate cross-linked polymer (A) obtained by such the surface cross-linking can be subjected to particle size adjustment by classification, if necessary. A weight average molecular weight of the resulting (A) is not almost changed from that before surface cross-linking and is preferably 100 to 800 μm, more preferably 200 to 500 μm. The (A) ground such that 95% by weight or more particles are in a range of 100 to 850 μm can be used. The content of fine particles is preferably low. Preferably, the content of particles of 100 μm or less is 3% or lower. More preferably, the content of particles of 150 μm or less is 3% or lower.

Such the surface-cross-linked type cross-linked polymer is excellent in the absorbing capacity not only under normal pressure but also under load, and has the large gel strength, being preferable.

In the cross-linked polymer (A) of the present invention, a cross-linked polymer (A2) obtained by polymerizing a vinyl series monomer (a) and an optional vinyl series monomer (a3), and a first cross-linking agent (b1) in the presence of at least 1 initiator (c) selected from the group consisting of an azo initiator, a peroxide initiator, a redox initiator and an organic halogenated initiator, and water, is preferably further surface-cross-linked with a second cross-linking agent (b2).

The present cross-linked polymer thus obtained can satisfy the following requirements ① to ③:
① (X)≧33 g/g
② (Y)≧25 g/g
③ (Y)≧−0.54(X)+42
wherein, (X) is an water retaining amount for a physiological saline after 1 hour absorption, and (Y) is an absorbing amount for a physiological saline after 1 hour under 60 g/cm² load.

The requirement ① relates to a water retaining amount of a cross-linked polymer and the requirement ② relates to an absorbing amount under high load. When these requirements are not satisfied, since a water retaining amount is small or an absorbing amount under load is small, the capacity as an absorbing article is lowered and, in particular, when applied to a thin type absorbing article, a problem on leakage occurs. The requirement ③ represents the balance between a water retaining amount and an absorbing amount under high load of a cross-linked polymer and, when the requirement ③ is not satisfied, an absorbing article having the excellent absorbing capacity can not be obtained.

The aforementioned requirements are satisfied, the excellent capacities as an absorbing article are manifested. In addition, the present cross-linked polymer thus obtained can satisfy the more preferable following requirement ③′ in place of the above requirement ③:
③′ (Y)≧−0.54(X)+42

Further, according to the aforementioned process, the present cross-linked polymer can satisfy the more preferable following requirements ①′ to ③″ in place of the above requirements ① to ③:
①′ (X)≧33 g/g
②′ (Y)≧25 g/g
③″ (Y)≧0.54(X)+42
③″ (Y)≧0.54(X)+42

In addition, the gel elasticity value of a 40-fold swollen gel of the cross-linked polymer (A) which has absorbed a physiological saline is preferably 3,000 N/m² or more, more preferably 4,000 N/m² or more, particularly preferably 5,000 to 200,000 N/m², most preferably 6,000 to 180,000 N/m².

When the gel elasticity value is 3,000 N/m² or more, the deformation or the rupture of the gel hardly occur upon application of shear to a water-absorbed gel, the repetition absorbing capacity upon long term use of an absorbing article to which a cross-linked polymer is not lowered, and the dry feeling is not lowered and the leakage dose not occur.

When the present cross-linked polymer (A) is applied to an absorbing structure or an absorbing article, from a viewpoint of workability, drape and resistance to moisture, the water content is preferably 2 to 10% by weight, more preferably 3 to 8% by weight, the dust occurrence is preferably 0 to 50 cpm, more preferably 0 to 30 cpm, an average particle size is preferably 200 to 500 μm, and the moisture absorbing blocking rate after standing at 40° C. for 3 hours under the relative humidity of 80% is preferably 0 to 50%, more preferably 0 to 20%.

The water content can be measured by a weight loss rate after the present cross-linked polymer (A) is drying-treated at 125° C. for 1 hour.

The dust occurrence is measured using a 1 liter suction bottle, a suction inlet and a digital dust occurrence measuring machine (manufactured by Shibatakagaku). A suction inlet of a suction bottle and a suction inlet of a digital dust occurrence measuring machine (manufactured by Shibatakagaku) are connected with a glass tube having an internal diameter of 7 mm and a length of 10 cm, 20 g of powders of the cross-linked polymer is dropped into a suction bottle through an upper port of a suction bottle using a funnel. The number of dusts occurred from the dropped powders of the cross-linked polymer during 1 minute is measured using a digital dust occurrence measuring machine, and this value is adopted as dust occurrence (unit; cpm).

In the present invention, a surfactant, a preservative (preservative such as salycilic acid, sorbic acid, dehydroacetic aicd, and methylnaphthoquinone, and germicide such as chloramine B and nitrofurazone), a mildenproofing agent (butyl p-oxybenzoate etc.), an antibacterial agent (benzalkonium chloride salt, glucronic acid chlorhexidine etc.), an antioxidant, an ultraviolet absorbing agent, a colorant (inorganic pigment such as titanium oxide and ferrite, organic pigment such as azo lake, benzoimidazolone and phthalocyanine, dye such as nigrocin and aniline), a flavor (natural perfume such as musk, abietic oil and turpentine oil, synthetic perfume such as menthol, citral, p-methylacetophenone and floral), a deodorant (zeolite, silica, flavonoid and cyclodextrin), an inorganic powder and an organic fibrous substance and the like can be added at an arbitral stage (before polymerization, during polymerization and after polymerization) in the present process, if necessary. An amount thereof is different depending upon the use and is preferably 0 to 20% by weight, more preferably 0 to 18% by weight based on the weight of the cross-linked polymer (A).

Examples of the surfactant include anionic surfactants, nonionic surfactants, cationic surfactants and amphoteric surfactants, for example, those described in U.S. Pat. No. 4,331,447, and these may be used alone or in combination of 2 or more of them.

Examples of anionic surfactants include hydrocarbon series ether carboxylic acid having the carbon number of 8 to 24 or salts thereof [polyoxyethylene (polymerization degree=1 to 100) lauryl ether acetate sodium, polyoxyethylene (polymerization degree=1 to 100) lauryl sulfosuccinate disodium etc.], hydrocarbon series sulfate ester salts having the carbon number of 8 to 24 [sodium lauryl sulfate, polyoxyethylene (polymerization degree=1 to 100) lauryl sulfate sodium, polyoxyethylene (polymerization degree=1 to 100) lauryl sulfate triethanolamine, polyoxyethylene (polymerization degree=1 to 100) coconut oil fatty acid monoethanolamide sulfate sodium], hydrocarbon series sulfonate salts having the carbon number of 8 to 24 [sodium dodecylbenzenesulfonate etc.], hydrocarbon series phosphate salts having the carbon number of 8 to 24 [sodium laurylphosphate, polyoxyethylene (polymerization degree=1 to 100) lauryl ether phosphate sodium etc.], fatty acid salts [sodium laurate, lauric acid triethanolamine etc.], acylated amino acid salts [coconut oil fatty acid methyl taurine sodium, coconut oil fatty acid sarcosine sodium, coconut oil fatty acid sarcosine triethanolamine, N-coconut oil fatty acid acyl-L-glutamic acid triethanolamine, N-coconut oil fatty acid acyl-L-glutamate sodium, lauroylmethyl-β-alanine sodium etc.], and others [sulfosuccinic acid polyoxyethylene (polymerization degree=1 to 100) lauroylethanolamide disodium etc.].

Examples of the noionic surfactants include fatty acid series alcohols (carbon number of 8 to 24) alkyleneoxide (carbon number of 2 to 8) adduct (polymerization degree=1 to 100) [lauryl alcohol ethylene oxide adduct (polymerization degree=20), oleyl alcohol ethylene oxide adduct (polymerization degree=10), sperm alcohol ethylene oxide adduct (polymerization degree=35) etc.], polyoxyalkylene (carbon number of 2 to 8, polymerization degree=1 to 100) higher fatty acid (carbon number of 8 to 24) ester [monostearic acid polyethylene glycol (polymerization degree=20), distearic acid polyethylene glycol (polymerization degree=30) etc.], polyhydric (2-hydric to 10-hydric or more-hydric) alcohol fatty acid (carbon number of 8 to 24) ester [monostearic acid glycerin, monostearic acid ethylene glycol, sorbitan lauric acid (mono/di) ester, sorbitan palmitic acid (mono/di) ester, sorbitan stearic acid (mono/di) ester, sorbitan oleic acid (mono/di) ester, sorbitan coconut oil (mono/di) ester stc.], polyoxyalkylene (carbon number of 2 to 8, polymerization degree=1 to 100) polyhydric (2-hydric to 10-hydric or more-hydric) alcohol higher fatty acid (carbon number of 8 to 24) ester [polyoxyethylene (polymerization degree=10) sorbitan lauric acid (mono/di) ester, polyoxyethylene (polymerization degree=20) sorbitan palmitic acid (mono/di) ester, polyoxyethylene (polymerization degree=15) sorbitan stearic acid (mono/di) ester, polyoxyethylene (polymerization degree=10) sorbitan optic acid (mono/di) ester, polyoxyethylene (polymerization degree=25) lauric acid (mono/di) ester, polyoxyethylene (polymerization degree=50) stearic acid (mono/di) ester, polyoxyethylene (polymerization degree=18) oleic acid (mono/di) ester, sorbitan, polyoxyethylene (polymerization degree=50) dioleic acid methyl glucoside etc.], fatty acid alkanolamide [1:1 type coconut oil fatty acid diethanolamide, 1:1 type luric acid diethanolamide etc.], polyoxyalkylene (carbon number of 2 to 8, polymerization degree=1 to 100), alkyl (carbon number of 1 to 22) phenylether(polyoxyethylene(polymerization degree=20) nonilphenylether etc.), polyoxyalkylene (carbon number of 2 to 8, polymerization degree=1 to 100), alkyl (carbon number of 8 to 24) aminoether and alkyl (carbon number of 8 to 24) dialkyl (carbon number of 1 to 6) amineoxide [lauryldimethylamincoxide etc.], polydimethylsiloxane polyoxyethylene adduct, polyoxyethylene polyoxypropylene block polymer (weight average molecular weight=150 to 10,000) and the like.

Examples of the cationic surfactants include quaternary ammonium salt type [stearyltrimethylammonium chloride, behenyltrimethylammonium chloride, distearyldimethylammonium chloride, ethyl sulfate lanolin fatty acid aminopropylethyldimethylammonium etc.], amine salt type [stearic diethylaminoethylamide lactate, dilaurylamine hydrochloride, oleylamine lactate etc.], and the like.

Examples of the amphoteric surfactants include betaine type amphoteric surfactants [coconut oil fatty acid amidopropyldimethylaminoacetic acid betaine, lauryldimethylaminoacetic acid betaine, 2-alkyl-N-carboxymethyl-N-hydroxyethylimidazolinium betaine, laurylhydroxysulfo betaine, lauroylamidoethylhydroxyethylcarboxymethyl betaine hydroxypropylphosphate sodium etc.], amino acid type amphoteric surfactants [β-laurylaminopropionate sodium etc.], and the like.

Examples of the antioxident include hindered phenol series antioxident such as triethyleneglycol-bis-[3-(3-t-butyl-5-methyl-4-hydroxyphenyl)propionate], 1,6-hexanediol-bis [3-(3,5-di-t-butyl-4-hydroxyphenyl) propionate], octadecyl-3-(3,5-di-t-butyl-4-hydroxyphenylpropionate, 3,5-di-t-butyl-4-hydroxybenzylphosphonate-diethyl ester and the like; amine series antioxidants such as n-butylamine, triethylamine, diethylaminomethyl methacrylate and the like, a combination of 2 or more of them.

Examples of the ultraviolet absorbing agent include benzotriazole series ultraviolet absorbing agents such as 2-(5-methyl-2-hydroxyphenyl)benzotriazole, 2-(3,5-di-t-butyl-2-hydroxyphenyl)benzotriazole, 2-(3,5-di-t-butyl-2-hydroxyphenyl)-5-chlorobenzotriazole, 2-(3,5-di-t-amyl-2-hydroxypehnyl)benzotriazole and the like; triazine series ultraviolet absorbing agents such as 2-(4,6-diphenyl-1,3,5-triazin-2-yl)-5-[(hexyl)oxy)-phenol and the like; benzophenone series ultraviolet absorbing agents such as 2-hydroxy-4-n-octyloxybenzophenone and the like; oxalic acid anilide series ultraviolet absorbing agents such as 2-ethoxy-2'-ethyloxalic acid bisanilide and the like, and a combination of 2 or more of them.

Examples of the inorganic powder include calcium carbonate, kaolin, talc, mica, bentonite, clay, sericite, asbestos, glass fiber, carbon fiber, glass powder, glass baloon, sand bar baloon, coal powder, metal powder, ceramic powder, silica, zeolite, slate powder and the like. The form thereof may be arbitrary and an average particle size is preferably 0.1 micron to 1 mm.

Examples of the pigment include carbon black, titanium oxide, red iron oxide, minium, parared, Prussian blue and the like.

Examples of the organic fibrous material include natural fibers [cellulose sereis (cotton, sawdust, straw etc.) and others, grass coal, wool, microfibril, bacterial cellulose etc.], artificial fibers (cellulose series such as rayon, acetate etc.), synthetic fibers (polyamide, polyester, acryl etc.), pulp [mechanical pulp (ground pulp from log, Asplund method ground pulp etc.), chemical pulp (sulfite pulp, soda pulp, sulfate pulp, nitric acid pulp, chlorine pulp etc.), semichemical pulp, regenerated pulp (for example, materials prepared by mechanically crushing or grinding papers once made from pulps, or regenerated wastepaper pulp prepared by mechanically crushing or grinding wastepapers etc.) and the like.

(Absorbing Structure and Absorbing Article)

The cross-linked polymer of the present invention is extremely excellent in the balance between the water retaining amount and the absorbing amount under load, and can be applied to various absorbing structures (C) and absorbing articles (D) to obtain articles excellent in the absorbing capacity.

In a method for applying the cross-linked polymer (A) to the absorbing structure (C), the obtained absorbing structure is composed of a matrix of the cross-linked polymer (A) and the fibrous material (B) and can be prepared by:

(1) dispersing the cross-linked polymer between fibrous layers comprising pulps, heat-adherable fibers and the like which are disposed at a layer form;

(2) mixing the fibrous material comprising pulps, heat-adherable fibers and the like, and the cross-linked polymer; or (3) sandwiching the cross-linked polymer with 2 or more absorbing papers or nonwoven cloths together with fibrous materials, if necessary.

Examples of the fibrous material (B) include fibrous materials which have previously been used in absorbing articles such as various fluffy pulps and cotton-like pulps, and raw materials (needle leaf, broadleaf tree etc.), manufacturing method [chemical pulp, semichemical pulp, chemithermomechanical pulp (CTMP) etc.] and bleaching method and the like are not particularly limited.

Alternatively, in addition to the aforementioned organic fibrous materials as a fibrous material, synthetic fibers which are not swollen in water may be used alone or in combination with the aforementioned fluffy pulps or cotton-like-pulps, if necessary. Examples of the synthetic fibers include polyolefin series fibers (for example, polyethylene series fibers, polypropylene series fibers), polyester series fibers (for example, polyethyleneterephthlate fibers), polyolefin-polyester composite fibers, polyamide sereis fibers, polyacrylonitrile series fibers.

The length and the thickness of the fibrous material (B) are not particularly limited, and it is usually suitable that the length is 1 to 200 mm and the thickness is 0.1 to 100 denier.

Also, the shape is not particularly limited as far as it is fibrous, and the examples of the shape include web-like, thin cylindrical, cut split yarn-like, staple like, filament-like and the like.

An amount of the cross-linked polymer (A) of the present invention to be added to the absorbing structure (C) can vary variously depending upon a kind and a size of the absorbing structure, and the goal absorbing capacity, and an amount of the cross-linked polymer (A) is preferably 30 to 95% by weight, more preferably 40 to 95% by weight relative to the weight of the absorbing structure (C).

Preferable absorbing articles of the present invention are absorbing articles (D) provided with the absorbing structure (C), a liquid permeable sheet and a breathable back sheet, more preferably absorbing articles (D) as a hygiene, particularly preferably paper diapers having the surface dryness value measured by the SDME method described below of 50% or more, more preferably 55% or more.

EXAMPLES

The present invention will be further explained by the following Examples and Comparative Examples but is not limited to them. In the present invention, the water retaining amount, the absorbing amount under load, the gel elasticity and the moisture absorbing blocking rate were measured according to the following methods. Percentage indicates % by weight unless otherwise indicated.

(Water Retaining Amount)

1.00 g of the cross-linked polymer powders were placed into a tea bag (longitudinal 20 cm and traverse 10 cm) made of a 250 mesh nylon net, immersed in 1,000 cc of a physioligical saline (sodium chloride concentration 0.9%) for 1 hour without stirring, suspended for 15 minutes to remove water, the tea bag as a whole was placed in a centrifugation machine, and centrifuged at 150 G for 90 seconds to dehydrate excess water. Again in the weight after centrifugation and dehydration was measured as water retaining amount. A temperature of the physiological saline used and a temperature for measurement were 25° C.

(Absorbing Amount Under Load)

0.10 g of the cross-linked polymer powders were placed into a cylindrical plastic tube (inner diameter 30 mm and height 60 mm) in which a 250 mesh nylon net was applied to the bottom to the uniform state, and a weight having an external diameter 30 mm was placed on this resin at a load of 60 g/cm$^2$.

The plastic tube in which the cross-linked polymer powders were placed was immersed into a laboratory dish (diameter: 12 cm) containing 60 ml of a physiological saline with a nylon net side down, which was allowed to stand. The increased weight that the cross-linked polymer absorbed a physiological saline was measured after 1 hour, and an 10-fold value of that value was adopted as the absorbing amount under load at 60 g/cm$^2$ conditions. A temperature of the physiological saline used and a temperature for measurement were 25° C.

(Gel Elasticity)

40 ml of a physiological saline was absorbed in 1.00 g of the cross-linked polymer powders to make a 40-fold swollen gel. 40 ml of a physiological saline was placed in a 100 ml beaker. 3 cm stirrer beads were placed, which was placed on a magnetic stirrer so that the stirrer beads are rotated at a center of the beaker. Rotation was performed at 600±10 rpm, the production of the stable eddy was confirmed. Then, 1.00 g of the cross-linked polymer powders were placed once, the rotation of the stirrer beads was stopped on the way, which was allowed to stand for 3 hours to make a swollen gel.

0.200 g of the swollen gel was on a center of a support table of a Theological measuring machine (manufactured by Yamaden; creepmeter RE-33005) and the surface thereof was made flat and smooth. Then, 30 g stress (P=30×98/S) was applied from the upper surface of the swollen gel, and a deformation rate (H=compression height/initial height) when pressurized with a cylinder was obtained. In addition, the cross-sectional area [S=sample volume/(initial height-compression height)] of the gel upon this was measured, and the gel elasticity value was obtained according to the following equation:

Gel elasticity (N/m²)=P/H

A temperature of the physiological saline, a temperature upon preparation of the swollen gel and a temperature for measurement were 25° C.

(Moisture Absorbing Blocking Rate)

10 g of the cross-linked polymer powders were placed uniformly into a dish made of aluminium having a diameter of 5 cm, and allowed to stand in a thermo-hygrostat at 40° C. and 80% relative humidity for 3 hours. After allowing to stand for 3 hours, the weight of the cross-linked polymer was measured and, thereafter, the powders were slightly classified with a 12 mesh wire net, the weight of the cross-linked polymer powder which did not pass 12 mesh due to blocking caused by moisture absorbing was measured, and the moisture absorbing blocking rate was obtained according to the following equation.

Moisture absorbing blocking rate=(weight of the cross-linked polymer which was left on a 12 mesh wire net after allowing to stand for 3 hours/total weight of the cross-linked polymer after allowing to stand for 3 hours)×100

Example 1

77 g of sodium acrylate, 22.85 g of acrylic acid, 0.15 g of N,N'-methylenebisacrylamide, 293 g of deionized water and 0.001 g of dichlorotris(triphenylphosphine) ruthenium were placed into a reaction vessel made of a glass having the volume of 1 liter, and a temperature of the contents was held at 3° C. while stirring and mixing.

Nitrogen was flown into the contents to adjust the dissolved oxygen amount to 1 ppm or less, 0.3 g of a 1% aqueous hydrogen peroxide solution, 0.8 g of a 0.2% aqueous ascorbic acid solution and 0.8 g of a 2% aqueous 2,2'-azobis(2-amidinopropane) dihydrochloride solution were added to mix to initiate polymerization, a temperature reached 69° C. after 1.5 hours, and polymerization was performed for a total of about 5 hours after initiation while holding at that temperature to obtain a hydrated gel-like polymer (A-1).

The resulting hydrated gel (A-1) was cut finely with an internal mixer, and dried with a breathable type band drier at 135° C. and a wind rate of 2.0 m/second.

The resulting dried material was ground, adjusted to 30 to 60 mesh particle size, 100 g of which was stirred at a high speed and, at the same time, 2 g of a solution of ethylene glycol diglycidyl ether in 10% water/methanol (water/methanol=70/30) was added to mix, and heat-cross-linked at 140° C. for 30 minutes to obtain the cross-linked polymer (1).

The particle size distribution and the evaluation results of this cross-linked polymer (1) are shown in Table 1. The moisture content of the cross-linked polymer (1) was 4%, and the dust occurrence was 10 cpm.

Example 2

81.7 g of acrylic acid, 0.15 g of N,N'-methylenebisacrylamide, 241 g of deionized water and 0.001 g of dichlorotris(triphenylphosphine) ruthenium were placed into a reaction vessel made of a glass having the volume of 1 liter, and a temperature of the contents was held at 3° C. while stirring and mixing.

Nitrogen was flown into the contents to adjust the dissolved oxygen amount to 1 ppm or less, 0.3 g of a 1% aqueous hydrogen peroxide solution, 0.8 g of a 0.2% aqueous ascorbic acid solution and 0.8 g of a 2% aqueous 2,2'-azobis(2-amidinopropane) dihydrochloride solution were added to mix to initiate polymerization, a temperature reached 74° C. after 1.5 hours, and polymerization was performed for total of about 5 hours after initiation while holding at that temperature to obtain a hydrated gel-like polymer.

While cutting finely this hydrated gel-like polymer with an internal mixer, 109.1 g of a 30% aqueous sodium hydroxide solution was added to knead to obtain the hydrated gel (A-2), 72 mol % of a carboxylic acid of which was neutralized.

The hydrated gel (A-2) was dried with a breathable type band drier at 140° C. and a wind rate of 2.0 m/second.

The resulting dried material was ground, adjusted to 30 to 60 mesh particle size, 100 g of which was stirred at a high speed and, at the same time, 2 g of a solution of ethylene glycol diglycidyl ether in 10% water/methanol (water/methanol=70/30) was added to mix, and heat-cross-linked at 140° C. for 30 minutes to obtain the surface-cross-linked type cross-linked polymer (2).

The particle size distribution and the evaluation results of this cross-linked polymer (2) are shown in Table 1. The moisture content of the cross-linked polymer (2) was 5%, and the dust occurrence was 11 cpm.

Example 3

77 g of sodium acrylate, 22.6 g of acrylic acid, 0.4 g of pentaerythritol triallyl ether, 293 g of deionized water and 0.001 g of dichlorotris(triphenylphosphine) ruthenium were placed into a reaction vessel made of a glass having the volume of 1 liter, and a temperature of the contents was held at 3° C. while stirring and mixing.

Nitrogen was flown into the contents to adjust the dissolved oxygen amount to 1 ppm or less, 0.3 g of a 1% aqueous hydrogen peroxide solution, 0.8 g of a 0.2% aqueous ascorbic acid solution and 0.8 g of a 2% aqueous 2,2'-azobis(2-amidinopropane) dihydrochloride solution were added to mix to initiate polymerization, a temperature reached 69° C. after 1.5 hours, and polymerization was performed for a total of about 5 hours after initiation while holding at that temperature to obtain a hydrated gel-like polymer (A-3).

The resulting hydrated gel (A-3) was cut finely with an internal mixer, and dried with a breathable type band drier at 135° C. and a wind rate of 2.0 m/second.

The resulting dried material was ground, adjusted to 30 to 60 mesh particle size, 100 g of which was stirred at a high speed and, at the same time, 2 g of a solution of ethylene glycol diglycidyl ether in 10% water/methanol (water/methanol=70/30) was added to mix, and heat-cross-linked at 140° C. for 30 minutes to obtain the cross-linked polymer (3).

The particle size distribution and the evaluation results of this cross-linked polymer (3) are shown in Table 1. The moisture content of the cross-linked polymer (3) was 4%, and the dust occurrence was 15 cpm.

Example 4

81.7 g of acrylic acid, 0.4 g of pentaerythritol triallyl ether, 241 g of deionized water and 0.001 g of dichlorotris(triphenylphosphine) ruthenium were placed into a reaction vessel made of a glass having the volume of 1 liter, and a temperature of the contents was held at 3° C. while stirring and mixing.

Nitrogen was flown into the contents to adjust the dissolved oxygen amount to 1 ppm or less, 0.3 g of a 1% aqueous hydrogen peroxide solution, 0.8 g of a 0.2% aqueous ascorbic acid solution and 0.8 g of a 2% aqueous 2,2'-azobis(2-amidinopropane) dihydrochloride solution were added to mix to initiate polymerization, a temperature reached 74° C. after 1.5 hours, and polymerization was performed for a total of about 5 hours after initiation while holding at that temperature to obtain a hydrated gel-like polymer.

While cutting finely this hydrated gel-like polymer with an internal mixer, 109.1 g of a 30% aqueous sodium hydroxide solution was added to knead to obtain the hydrated gel (A-4), 72 mole % of a carboxylic acid of which was neutralized.

The hydrated gel (A-4) was dried with a breathable type band drier at 140° C. and a wind rate of 2.0 m/second.

The resulting dried material was ground, adjusted to 30 to 60 mesh particle size, 100 g of which was stirred at a high speed and, at the same time, 2 g of a solution of ethylene glycol diglycidyl ether in 10% water/methanol (water/methanol=70/30) was added to mix, and heat-cross-linked at 140° C. for 30 minutes to obtain the surface-cross-linked type cross-linked polymer (4) was obtained.

The particle size distribution and the evaluation results of this cross-linked polymer (4) are shown in Table 1. The moisture content of the cross-linked polymer (4) was 6%, and the dust occurrence was 20 cpm.

Example 5

According to the same manner as that of Example 1 except that 0.17 g of N,N'-methylenebisacrylamide, the surface-cross-linked type cross-linked polymer (5) was obtained.

The particle size distribution and the evaluation results of this cross-linked polymer (5) are shown in Table 1. The moisture content of the cross-linked polymer (5) was 8%, and the dust occurrence was 9 cpm.

Example 6

According to the same manner as that of Example 2 except that 0.3 g of a 1% aqueous potassium persulfate was used in place of 0.3 g of a 1% aqueous hydrogen peroxide, the surface-cross-linked type cross-linked polymer (6) was obtained.

The particle size distribution and the evaluation results of this cross-linked polymer (6) are shown in Table 2. The moisture content of the cross-linked polymer (6) was 6%, and the dust occurrence was 18 cpm.

Example 7

According to the same manner as that of Example 4 except that 0.5 g of pentaerythritol triallyl ether was used in place of 0.4 g of pentaerythritol triallyl ether, 375 g of deionized water was used in place of 241 g of deionized water, 1.0 g of a 2% aqueous 2,2'-azobis(2-amidinopropane) dihydrochloride was used in place of 0.8 g of 20% 2,2'-azobis(2-amidinopropane) dihydrochloride, and dichlorotris(triphenylphosphine) ruthenium was not used, the surface-cross-linked type cross-linked polymer (7) was obtained.

The particle size distribution and the evaluation results of this cross-linked polymer (7) are shown in Table 2. The moisture content of the cross-linked polymer (7) was 8%, and the dust occurrence was 18 cpm.

Reference 2

121.2 g of cyclohexane was placed in a four-necked round flask, having the volume of 500 ml, equipped with a stirrer, a reflux condenser, a thermometer and a nitrogen gas introducing tube, 0.9 g of sorbitan monostearate was added to dissolve it, a nitrogen gas was blown therin to expel the dissolved oxygen. Separately, 70.0 g of a 25% aqueous sodium hydroxide solution was added to a mixture of 45 g of acrylic acid and 6.4 g of water under ice-cooling to neutralize 70% of a carboxyl group in a conical beaker having the volume of 300 ml. Then, 0.033 g of N,N'-methylenebisacrylamide as a cross-linking agent, 0.0546 g of sodium hypophosphite as a water-soluble chain transfer agent and 0.0313 g of 2,2'-azobis(2-amidinopropane) dihydrochloride as an initiator were added to dissolve them. The contents of this conical beaker having the volume of 300 ml was added to the contents of the aforementioned four-neck round flask, stirred to disperse them, an internal temperature of the flask was raised with an oil bath while bubbling a nitrogen gas, an internal temperature was held at 60° C., and polymerization was performed for 2 hours while stirring. The contents after 2 hours became the slurry-like in which the cross-linked polymer swollen with water was dispersed in cyclohexane. Then, a temperature of the oil bath was raised, and dehydration was performed to the water of the swollen cross-linked polymer of 20%, by azeotropy with cyclohexane in the flask. After dehydration, stirring was stopped, and the swollen polymer particles were settled to the bottom of the round flask, which could be therefore easily separated from the cyclohexane phase by decantation. The separated swollen polymer was transferred to a reduced pressure drier, which was heated to 80 to 90° C. to remove the attached cyclohexane and water, to obtain the dry cross-linked polymer particles. While stirring 30 g of the particles at a high speed, 0.6 g of a solution of ethylene glycol diglycidyl ether in 10% water/methanol (water/methanol=70/30) was added to mix, and heat-cross-linked at 140° C. for 30 minutes to obtain the surface-cross-linked type cross-linked polymer (8).

The particle size distribution and the evaluation results of this cross-linked polymer (8) are shown in Table 2. The moisture content of the cross-linked polymer (8) was 5%, and the dust occurrence was 18 cpm.

Comparative Example 1

77 g of sodium acrylate, 22.7 g of acrylic acid, 0.3 g of N,N'-methylenebisacrylamide and 295 g of deionized water were placed into a reaction vessel made of a glass having the volume of 1 liter, and a temperature of the contents was held at 3° C. while stirring and mixing.

Nitrogen was flown into the contents to adjust the dissolved oxygen amount to 0.3 ppm or less, 1 g of a 1% aqueous hydrogen peroxide solution, 1.2 g of a 0.2% aqueous ascorbic acid solution and 2.8 g of a 2% aqueous 2,2'-azobis(2-amidinopropane) dihydrochloride solution were added to mix to initiate polymerization, a temperature reached 70° C. after 1.5 hours, and polymerization was performed for a total of about 5 hours after initiation while holding at that temperature to obtain a hydrated gel-like polymer (A-1).

The resulting hydrated gel (A-1) was cut finely with an internal mixer, and dried with a breathable type band drier at 135° C. and a wind rate of 2.0 m/second.

The resulting dried material was ground, adjusted to 30 to 60 mesh particle size, 100 g of which was stirred at a high speed and, at the same time, 1 g of a solution of ethylene glycol diglycidyl ether in 10% water/methanol (water/methanol=70/30) was added to mix, and heat-cross-linked at 140° C. for 30 minutes to obtain the comparative cross-linked polymer (1').

The particle size distribution and the evaluation results of this comparative cross-linked polymer (1') are shown in Table 2.

Comparative Example 2

81.7 g of acrylic acid, 0.2 g of N,N'-methylenebisacrylamide and 241 g of deionized water were placed into a reaction vessel made of a glass having the volume of 1 liter, and a temperature of the contents was held at 3° C. while stirring and mixing.

Nitrogen was flown into the contents to adjust the dissolved oxygen amount to 0.3 ppm or less, 1 g of a 1% aqueous hydrogen peroxide solution, 1.2 g of a 0.2% aqueous ascorbic acid solution and 0.8 g of a 2% aqueous 2,2'-azobis(2-amidinopropane) dihydrochloride solution were added to mix to initiate polymerization, a temperature reached 75° C. after 1.5 hours, and polymerization was performed for total of about 5 hours after initiation while holding at that temperature to obtain a hydrated gel-like polymer.

While cutting finely this hydrated gel-like polymer with an internal mixer, 109 g of a 30% aqueous sodium hydroxide solution was added to knead to obtain the hydrated gel (A-2), 71 mol % of a carboxylic acid of which was neutralized.

The hydrated gel (A-2) was dried with a breathable type band drier at 140° C. and a wind rate of 2.0 m/second.

The resulting dried material was ground, adjusted to 30 to 60 mesh particle size, 100 g of which was stirred at a high speed and, at the same time, 1 g of a solution of ethylene glycol diglycidyl ether in 10% water/methanol (water/methanol=70/30) was added to mix, and heat-cross-linked at 140° C. for 30 minutes to obtain the surface-cross-linked type comparative cross-linked polymer (2').

The particle size distribution and the evaluation results of this comparative cross-linked polymer (2') are shown in Table 2.

(Evaluation of a Paper Diaper)

Absorbing structures were made using the present cross-linked polymers (1) to (6) and comparative cross-linked polymers (1') and (2'), and an absorbing amount under load, an absorbing rate under load, a diffusion area under load, the surface dry feeling and the surface dryness value by SDME of paper diapers made according to the method below were measured by the following method. Percentage denotes % by weight unless indicated otherwise.

(Absorbing Amount Under Load)

An acrylic plate (weight 0.5 Kg) having the same area as that of the above paper diaper (140 mm×360 mm) in which a cylinder (internal diameter 3 cm, length 20 cm) is provided on its center was placed on a paper diaper, and a 20 Kg load is placed uniformly on the aclylic plate (total load 20.5 Kg). 80 ml of an artificial urine is poured in the cylinder. After 5 minutes, another 80 ml of a second time artificial urine is poured. Similarly, after 5 minutes, 80 ml of a third time artificial urine is poured, and allowed to stand for 5 minutes. The load and the acrylic plate were removed, the artificial urine which has not been absorbed by the paper diaper was removed, and weight (Wg) of a wet sample is measured. W is adopted as an absorbing amount under load.

(Absorbing Rate Under Load)

An acrylic plate (weight 0.5 Kg) having the same area as that of the above paper diaper (140 mm×360 mm) in which a cylinder (internal diameter 3 cm, length 20 cm) is provided on its center was placed on a model paper diaper, and a 20 Kg load is placed uniformly on the aclylic plate (total load 20.5 Kg). 80 ml of an artificial urine (colored with a blue ink) is poured in the cylinder. After 10 minutes, another 80 ml of a second time artificial urine is poured. Similarly, after 10 minutes, 80 ml of a third time artificial urine is poured, this third time absorbing time is measured and this is adopted as an absorbing rate under load.

(Diffusion Area Under Load)

After a third time absorbing rate was measured, an area in which an artificial urine was absorbed and spread in a horizontal direction is measured, which was adopted as diffusion area under load.

(Surface Dry Feeling)

After a diffusion area was measured, the dry feeling of the surface of a model paper diaper was determined by the finger touch of 10 panders and evaluated by the following 3 stages. An average of 10 panders was obtained, which was adopted as the surface dryness.

○: Better dry feeling,

Δ: Slightly wet but satisfactory level of dry feeling

X; Deficient in dry feeling, wet state, or no dry feeling, wet state, (Dryness Value by SDME Measuring Method)

The dryness value by SDME measuring method was measured using the SDME(Surface Dryness Measurement Equipment) testing machine (manufactured by WK system) according to the following procedures.

A detector of the SDME testing machine was placed on a sufficiently wetted paper diaper, the 0% dryness value was set and, then, a detector of the SDME testing machine was placed on a dry paper diaper, the 100% dryness was set, thus, the SDME testing machine was calibrated.

Then, a metal ring (diameter 70 mm) was set at a center or a paper diaper to be measured, and 80 ml of an artificial urine was poured. Immediately after pouring, the metal ring was removed, and the SDME detector was set at a center of the paper diaper to initiate measurement. After initiation of measurement, a value after 5 minutes was adopted as the dryness value by SDME.

Examples of 9 to 16

A mixture obtained by mixing 100 parts of a fluffy pulp, and each 100 parts of the present cross-linked polymers (1) to (6) obtained in Examples 1 to 8 with an air stream type mixing apparatus was uniformly layered to a basis weight of about 400 g/cm$^2$, which was pressed at a pressure of 5 Kg/cm$^2$ for 30 seconds to obtain absorbing structures (B1) to (B8) of Examples 9 to 16.

Example 17

A layer of 50 parts of a fluffy pulp was formed, 100 parts of the cross-linked polymer (2) obtained in Example 2 was uniformly scattered thereon, a layer of 50 parts of a fluffy pulp was further laminated thereon to obtain a sandwich structure, which was pressed at the pressure of 5 Kg/cm$^2$ for 30 seconds to obtain an absorbing structure (C2).

Comparative Examples 3 and 4

A mixture obtained by mixing 100 parts of a fluffy pulp and comparative cross-linked polymers (1') and (2') obtained in Comparative Examples 1 and 2 with an air stream type mixing apparatus was uniformly layered to a basis weight of about 400 g/cm$^2$, which was pressed at a pressure of 5 Kg/cm$^2$ for 30 seconds to obtain comparative absorbing structures (B1') and (B2') of Comparative examples 3 and 4.

Test Example

Absorbing structures obtained in Examples 9 to 16 and 17 and Comparative Examples 3 and 4 were cut into rectangle (14 cm×36 cm), a water absorbing paper (basis weight 15.5 g/m²) having the same size as that of the absorbing structure was arranged on the top and the bottom of each rectangle, a polyethlene sheet used for a commercially available paper diaper was arranged on the back and non-woven cloth (basis weight 20.0 g/m²) was arranged on the surface to make a paper diaper. An absorbing amount under load, an absorbing rate under load, a diffusion area under load, a surface dry feeling, and a surface dryness value by SDME of the paper diaper were evaluated. The results are shown in Table 3.

INDUSTRIAL APPLICABILITY

The cross-linked polymer of the present invention exerts the following effects:

① The balance of the water retaining capacity and the absorbing capacity under load is extremely excellent, and the dry feeling is exhibited even after water absorption.

② When the cross-linked polymer of the present invention is applied to hygiene articles such as paper diaper, physiological napkin and the like, not only the excellent absorbing capacity but also the excellent characteristics that an absorbed solution is hardly reverted even under pressure are exhibited.

Examples of hygiene articles include a paper diaper (paper diaper for children, paper diaper for adults etc.), a napkin (physiological napkin etc.), a paper towel, a pad (pad for incontinentia, underpad for operation etc.), a pet sheet (pet urine absorbing sheet) and the like.

The present invention (A) is also useful for various uses such as a urine gelling agent for a portable toilet, an agent for retaining freshness of vegetables and fruits, a drip absorbing agent for meats, fish and shellfish, a heat insulation material, disposable body warmer, a gelling agent for a cell, a water retaining agent for plants and soils, a moisture condensation preventing agent, a waterstop and a packing material, an artificial snow and the like in addition to the uses for aforementioned hygiene articles.

TABLE 1

| | | Example | | | | |
|---|---|---|---|---|---|---|
| | | 1 | 2 | 3 | 4 | 5 |
| Particle size (%) | 850 μm or more | 0.0 | 0.0 | 0.0 | 0.0 | 0.0 |
| | 850 to 710 μm | 0.1 | 0.1 | 0.1 | 0.1 | 0.1 |
| | 710 to 500 μm | 9.3 | 14.9 | 19.3 | 18.1 | 15.2 |
| | 500 to 300 μm | 56.6 | 56.6 | 57.5 | 55.3 | 56.4 |
| | 300 to 150 μm | 22.4 | 26.6 | 22.0 | 22.4 | 26.5 |
| | Less than 150 μm | 1.6 | 1.8 | 1.1 | 2.1 | 1.8 |
| Average particle size (μm) | | 363 | 365 | 362 | 354 | 364 |
| Gel elasticity (N/m²) | | 13,000 | 14,000 | 12,000 | 13,000 | 13,000 |
| Moisture absorbing blocking rate (%) | | 18 | 19 | 19 | 20 | 19 |
| Water retaining amount (g/g) | | 36 | 36 | 35 | 35 | 36 |
| Requirement ① | | Satisfactory | Satisfactory | Satisfactory | Satisfactory | Satisfactory |
| Absorbing amount under 60 g/cm² load (g/g) | | 26 | 27 | 25 | 26 | 26 |
| Requirement ② | | Satisfactory | Satisfactory | Satisfactory | Satisfactory | Satisfactory |
| Requirement ③ | | Satisfactory | Satisfactory | Satisfactory | Satisfactory | Satisfactory |

TABLE 2

| | | Example | | | Comparative Example | |
|---|---|---|---|---|---|---|
| | | 6 | 7 | 8 | 1 | 2 |
| Particle size (%) | 850 μm or more | 0.0 | 0.0 | 0.6 | 0.0 | 0.0 |
| | 850 to 710 μm | 0.1 | 0.1 | 0.1 | 0.1 | 0.1 |
| | 710 to 500 μm | 14.8 | 18.1 | 4.8 | 16.1 | 20.2 |
| | 500 to 300 μm | 56.7 | 55.3 | 83.7 | 57.5 | 59.6 |
| | 300 to 150 μm | 26.5 | 22.4 | 10.6 | 24.3 | 19.1 |
| | Less than 150 μm | 1.9 | 2.1 | 0.3 | 2.1 | 1.0 |
| Average particle size (μm) | | 363 | 354 | 363 | 350 | 366 |
| Gel elasticity (N/m²) | | 13,000 | 11,000 | 10,000 | 10,000 | 9,000 |
| Moisture absorbing blocking rate (%) | | 19 | 20 | 19 | 61 | 62 |
| Water retaining amount (g/g) | | 35 | 35 | 36 | 35 | 35 |
| Requirement ① | | Satisfactory | Satisfactory | Satisfactory | Satisfactory | Satisfactory |
| Absorbing amount under 60 g/cm² load (g/g) | | 25 | 23 | 22 | 21 | 20 |
| Requirement ② | | Satisfactory | Satisfactory | Satisfactory | Satisfactory | Satisfactory |
| Requirement ③ | | Satisfactory | Satisfactory | Satisfactory | Not Satisfactory | Not satisfactory |

TABLE 3

| Example | Absorbing structure used in paper diaper | Capacity of paper diaper | | | | |
|---|---|---|---|---|---|---|
| | | Absorbing amount under load (g/sheet) | Absorbing Rate under load (second) | Diffusion area under load (cm$^2$) | Surface dry feeling | SDME surface dryness value (%) |
| 9 | B1 | 287 | 355 | 444 | ◯ | 75 |
| 10 | B2 | 266 | 362 | 437 | ◯ | 65 |
| 11 | B3 | 272 | 341 | 450 | ◯ | 70 |
| 12 | B4 | 259 | 353 | 458 | ◯ | 62 |
| 13 | B5 | 263 | 341 | 440 | ◯ | 68 |
| 14 | B6 | 277 | 344 | 445 | ◯ | 71 |
| 15 | B7 | 251 | 365 | 440 | ◯ | 60 |
| 16 | B8 | 247 | 380 | 441 | ◯ | 57 |
| 17 | C2 | 303 | 321 | 427 | ◯ | 80 |
| Comparative Example | | | | | | |
| 3 | B1' | 225 | 397 | 382 | Δ | 43 |
| 4 | B2' | 218 | 411 | 390 | Δ | 36 |

What is claimed is:

1. A cross-linked polymer (A), which comprises 1 or 2 or more vinyl series monomers (a) selected from the group consisting of a water-soluble vinyl series monomer and a monomer which becomes water-soluble by hydrolysis, and a cross-linking agent (b) as an essential component components, wherein said cross-linked polymer satisfies the following requirements 1 to 3:

$(X) \geq 33$ g/g,   1

$(Y) \geq 25$ g/g,   2

$(y) \geq -0.54(X)+42$   3 wherein, (X) is a water retaining amount for a physiological saline after 1 hour absorption, and (Y) is an absorbing amount under 60 g/cm$^2$ load for a physiological saline after 1 hour;

wherein said vinyl series monomer (a) is a water-soluble vinyl series monomer selected from (a1) having at least one functional group selected from the group consisting of carboxylic acid (carboxylate) group, sulfonic acid (sulfonate) group, sulfuric acid (sulfate) group, phosphoric acid (phosphate) group, hydroxy group, amido group, and quaternary ammonium salt group, a vinyl series monomer (a2) which becomes water soluble by hydrolysis, and which has at least one functional group selected from the group consisting of acid anhydride group, lower alkyl ester group, and nitrile group, or a combination of them.

2. The cross-linked polymer according to claim 1, wherein the gel elasticity of a 40-fold swollen gel of said cross-linked polymer (A) with a physiological saline absorbed therein is 3,000 N/m$^2$ or more.

3. The cross-linked polymer according to claim 1, wherein said cross-linked polymer (A) is obtained by polymerizing the vinyl series monomer (a) and, if necessary, other vinyl series monomer (a3) selected from the group consisting of (i) aromatic ethylenic monomers having the carbon number of 8–30: (ii) aliphatic ethylenic monomers having the carbon number of 2 to 20; (iii) alicyclic ethylenic monomers having the carbon number of 5 to 15; (iv) (meth)acrylic acid esters having an alkyl group having the carbon number of 4 to 50, and a first cross-linking agent (b1) in the presence of 1 or 2 or more initiators (c) selected from the group consisting of azo series initiator, peroxide series initiator, redox series initiator and organic haloganated compound initiator, and water, to obtain a cross-linked polymer (A2) which is further surface-cross-linked with a second cross-linking agent (b2).

4. The cross-linked polymer according to claim 3, herein an amount of said first cross-linking agent (b1) is 0.001 to 5.0% by weight based on the weight of said vinyl series monomer (a) or a total weight of said vinyl sereis monomer (a) and said vinyl series monomer (a3).

5. The cross-linked polymer according to claim 3, wherein an amount of said second cross-linking agent (b2) is 0.001 to 7.0% by weight based on the weight of said vinyl series monomer (a) or a total weight of said vinyl series monomer (a) and said vinyl series monomer (a3).

6. The cross-linked polymer according to claim 1, wherein said cross-linked polymer (A) is obtained by polymerization at the concentration of a total weight of said vinyl series monomer (a) and the cross-linking agent (b) in a polymerization solution of 20% by weight or less.

7. The cross-linked polymer according to claim 1, wherein said cross-linked polymer (A) is obtained by polymerization at a polymerization temperature of 60° C. or lower and a temperature controlling width of ±5° C.

8. The cross-linked polymer according to claim 1 or 3, wherein said cross-linked polymer (A) is obtained by polymerization in the presence of a complex compound (d) of a metal element (d1) and a ligand (d2) of an anion or a neutral molecule.

9. The cross-linked polymer according to claim 8, wherein said metal element (d1) is a metal element selected from IB group and 4 to 6 Period VIII group in long-form Periodic Table of elements.

10. The cross-linked polymer according to claim 8, wherein an amount of the complex compound (d) is 0.005 ppm to 2% by weight and amount of said metal element (d1) is 0.001 ppm to 1% by weight based on a total weight of said vinyl series monomer (a) and the cross-linking agent (b) or a total weight of said vinyl series monomer (a), said vinyl series monomer (a3) and said cross-linking agent (b).

11. The cross-linked polymer according to claim 8, wherein the ligand (d2) of said anion or a neutral molecule is 1 or 2 or more selected from the group consisting of the following (1) to (3):

(1) an anion of an atom selected from hydrogen and halogen, (2) a compound having 1 or more atoms selected from the group consisting of nitrogen, oxygen, phosphorous and sulfur, (3) a conjugated system compound.

12. The cross-linked polymer according to claim 8, wherein said metal element (d1) is selected from 5 Period VIII group elements and the ligand (d2) of said anion or a neutral molecule is selected from the group consisting of a halogen ion, a tertiary phosphine compound and a combination of them.

13. The cross-linked polymer according to claim 1, wherein said cross-linked polymer (A) has the water content of 2 to 10% by weight, the dust occurrence of 0 to 50 cpm, an average particle size of 200 to 500 $\mu$m and the moisture absorbing blocking rate after allowing to stand at 40° C. and the relative humidity 80% for 3 hours of 0 to 50%.

14. The cross-linked polymer according to claim 1, wherein said cross-linked polymer (A) contains 1 or 2 or more additives (e) selected from the group consisting of surfactant, preservative, mildewproofing agent, antibacterial agent, antioxidant, ultraviolet absorbing agent, colorant (pigment, dye), flavor, deodorant, inorganic powder and organic fibrous material.

15. A process for producing a cross-linked polymer as defined in claim 3, which comprises polymerizing 1 or 2 or more said vinyl series monomers (a) selected from the group consisting of a water-soluble vinyl series monomer and a vinyl series monomer which becomes water-soluble by hydrolysis, and a first cross-linking agent (b1) with or without another vinyl series monomer (a3) in the presence of 1 or 2 or more said initiators (c) selected from the group consisting of azo series initiator, peroxide series initiator, redox series initiator and organic halogenated compound initiator, and water, to obtain a cross-linked polymer (A2) which is further surface-cross-linked with a second cross-linking agent (b2).

16. The process for producing a cross-linked polymer according to claim 15, wherein polymerization is performed in the presence of said complex compound (d) of said metal element (d1) and said ligand (d2) of an anion or a neutral molecule.

17. The process for producing a cross-linked polymer according to claim 16, wherein said metal element (d1) is a metal element selected from IB group and 4 to 6 Period VIII group in long-form Periodic Table of elements.

18. The process for producing cross-linked polymer according to claim 16, wherein said ligand (d2) of an anion or a neutral molecule is 1 or 2 or more selected from the group consisting of the following (1) to (3):

(1) an anion of an atom selected from hydrogen and halogen, (2) a compound having 1 or more atoms selected from the group consisting of nitrogen, oxygen, phosphorus and sulfur, (3) a conjugated system compound.

19. The process for producing a cross-linked polymer according to claim 16, wherein said metal element (d1) is selected from 5 Period VIII group elements and said ligand (d2) of an anion or a neutral molecule is a halogen ion, a tertiary phosphine compound or a combination of them.

20. The process for producing a cross-linked polymer according to claim 16, wherein an amount of said first cross-linking agent (b1) is 0.001 to 5.0% by weight based on the weight of said vinyl series monomer (a) or a total weight of said vinyl series monomer (a) and said vinyl series monomer (a3).

21. The process for producing a cross-linked polymer according to claim 16, wherein an amount of said second cross-linking agent (b2) is 0.001 to 7.0% by weight based on the weight of said vinyl series monomer (a) or the total weight of said vinyl series monomer (a) and said vinyl series monomer (a3).

22. The process for producing cross-linked polymer according to claim 16, wherein an amount of said initiator (c) is 0.005 to 0.5% by weight based on a total weight of the vinyl series monomer (a) and the cross-linking agent (b) or the total weight of the vinyl series monomer (a), the vinyl series monomer (a3) and the cross-linking agent (b).

23. An absorbing structure (C), which comprises a matrix of the cross-linked polymer (A) as defined in claim 1 and a fibrous material (B), the cross-linked polymer (A) being present in an amount of 30 to 95% by weight relative to the absorbing structure C.

24. An absorbing article, which comprises said absorbing structure (C) as defined in claim 23, liquid permeable sheet and a breathable back sheet.

25. The absorbing article according to claim 24, which is a hygiene article, selected from the group consisting of a paper diaper, a physiological napkin, a pad, a paper towel and a pet sheet.

26. A paper diaper according to claim 25, which has the surface dryness value measured by SDME of 50% or more.

* * * * *